(12) United States Patent
Yoon et al.

(10) Patent No.: US 11,497,216 B2
(45) Date of Patent: Nov. 15, 2022

(54) PSEUDOMONAS AERUGINOSA BACTERIOPHAGE PSE-AEP-4 AND USE THEREOF FOR INHIBITING PROLIFERATION OF PSEUDOMONAS AERUGINOSA

(71) Applicant: Intron Biotechnology, Inc., Gyeonggi-do (KR)

(72) Inventors: Seong Jun Yoon, Seoul (KR); Soo Youn Jun, Seoul (KR); Jee Soo Son, Seoul (KR); Hyoun Rok Paik, Incheon (KR); Hee Jeong Shin, Gyeonggi-do (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 616 days.

(21) Appl. No.: 16/486,595

(22) PCT Filed: Jan. 11, 2018

(86) PCT No.: PCT/KR2018/000508
§ 371 (c)(1),
(2) Date: Aug. 16, 2019

(87) PCT Pub. No.: WO2018/151417
PCT Pub. Date: Aug. 23, 2018

(65) Prior Publication Data
US 2019/0359949 A1  Nov. 28, 2019

(30) Foreign Application Priority Data
Feb. 17, 2017 (KR) .................. 10-2017-0021317

(51) Int. Cl.
*A61K 35/76* (2015.01)
*A01N 63/40* (2020.01)
(Continued)

(52) U.S. Cl.
CPC .............. *A01N 63/40* (2020.01); *A61K 35/76* (2013.01); *A61K 45/06* (2013.01); *A61P 31/04* (2018.01);
(Continued)

(58) Field of Classification Search
CPC .......... A61K 35/76; A61K 45/06; C12N 7/00; C12N 2795/10231; C12N 2795/10232; C12N 2795/10211; A61P 31/04
See application file for complete search history.

(56) References Cited

FOREIGN PATENT DOCUMENTS

| KR | 20120067096 A | 6/2012 |
|---|---|---|
| KR | 20130087118 A | 8/2013 |
| WO | WO-2018/151417 A1 | 8/2018 |

OTHER PUBLICATIONS

Bae, H.-W et al., "Complete Genome Sequence of Pseudomonas aeruginosa Podophage MPK7, Which Requires Type IV Pili for Infection", Genome Announcements, 2013. vol. 1, No. 5, document No. e00744-13.

(Continued)

*Primary Examiner* — Allison M Fox
*Assistant Examiner* — Qing Xu
(74) *Attorney, Agent, or Firm* — Ballard Spahr LLP

(57) ABSTRACT

The present invention relates to Podoviridae bacteriophage Pse-AEP-4 (accession number: KCTC 13166BP) isolated from nature, the Podoviridae bacteriophage Pse-AEP-4 having the capability to specifically kill *Pseudomonas aeruginosa* and having a genome represented by SEQ ID NO: 1, and a method for preventing or treating diseases induced by *Pseudomonas aeruginosa* by using a composition containing the Podoviridae bacteriophage Pse-AEP-4 as an active ingredient.

1 Claim, 2 Drawing Sheets
Specification includes a Sequence Listing.

(51) Int. Cl.
*A61P 31/04* (2006.01)
*A61K 45/06* (2006.01)
*C12N 7/00* (2006.01)

(52) U.S. Cl.
CPC ...... *C12N 7/00* (2013.01); *C12N 2795/10211* (2013.01); *C12N 2795/10231* (2013.01); *C12N 2795/10232* (2013.01); *C12N 2795/10271* (2013.01)

(56) References Cited

OTHER PUBLICATIONS

Cao, Z.0 et al., "Isolation and Characterization of a sphiKNIV-like1 Bacteriophage and Its Therapeutic Effect on Mink Hemorrhagic Pneumonia", PLoS One, 2015, vol. 10, No. 1. document No. e0116571, pp. 1-17.
International Search Report and Written Opinion were dated Apr. 26, 2018 by the International Searching Authority for International Application No. PCT/KR2018/000508, filed on Jan. 11, 2018 and published as WO 2018/151417 on Aug. 23, 2018 (Applicant-Intron Biotechnology, Inc.) (Original—10 Pages/Translation—3 Pages).
NCBI, GenBank Accession No. JX501340.1, "Pseudomonas Phage MPK7, Complete Genome", Oct. 24, 2013.
NCBI, GenBank Accession No. KM067278.1, "Pseudomonas Phage vB_PaeP_PPA-ABTNL, Complete Genome". Feb. 8, 2015.

[FIG. 1]
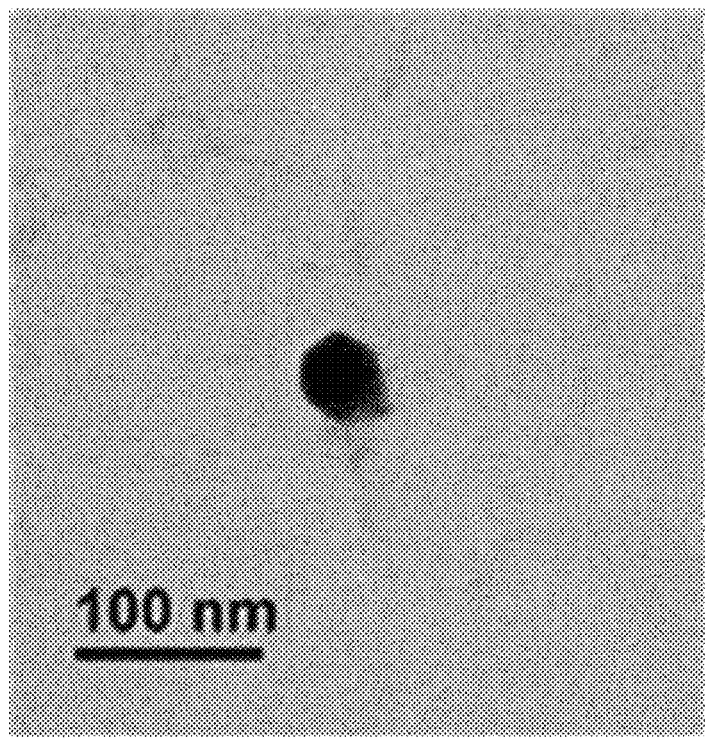

[FIG. 2]
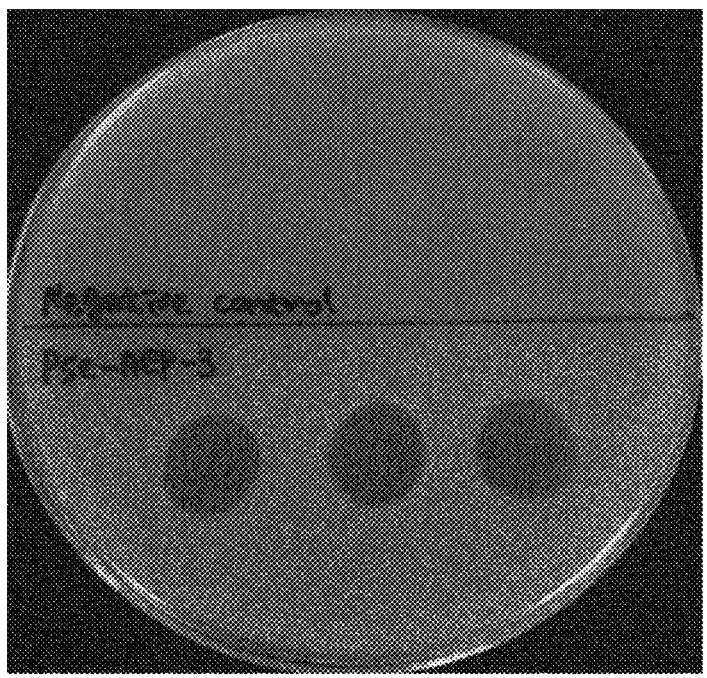

SEQUENCE LISTING

<160> NUMBER OF SEQ ID NOS: 1

<210> SEQ ID NO 1
<211> LENGTH: 43063
<212> TYPE: DNA
<213> ORGANISM: seudomonas aeruginosa bacteriophage Pse-AEP-4

<400> SEQUENCE: 1

```
ggcggagggg ttgatctcct gggccgaggc cacctgttcg aagatgctgt tcagcgtgtt      60
gaccagctcc gggtttgcct cgccttcctt ggcggcctgg atcatgcgca ccgcgctgcc     120
cacggactcg ccgtaggtct tggggaaggt ccccaggcgc aggccgagct gtgtgccctg     180
cacgagacgg tcagtaaggc ttgagccgtt ggcggcctgc atcttgtccc actgctccag     240
cgcctcggtg acgttggtac ccagcgtgtg gagggcgttg atgtctccgg cttccaaggc     300
cgccatgatg ccctgcatgc gctgagcgtt gcccaggccg gtcatggcct tggtcatgaa     360
cgagatggcc tgagcgtcgc tccagcggcc ctcctcgacc atgcctcgtg agtacgcctc     420
aacctcggca aggtctgtga tggctccgtt ggccaccgc  tgctggaagt ccgcgtcggc     480
ccgcagggta gccatcgatt ccttggcacg ggtctgtgcc ttcgattttt catagaggcc     540
```

```
gttgagcgca cgccggtcgt caaaggacat actgtccagg aacccggcat cgcgcaggcc    600
ctcatagatg ccccgctggt tcatgtccag gctggccgcc aggaactgca tgcctacctt    660
gtcgcgcacc tccagcggga tatcctcgga ggtcatgatg ttggtataga acaggccggc    720
ctcttccagg ctgagttgcc gggacagttc gtcgccggtg gcctgagcct gcacagcctt    780
ggccaggatg ctgttaccct gggtgcggaa gccacgggcg gcctggtcga tggaccagtc    840
catgtacgcc ttagcctgca tgccgaagag ctgttcctcg gccttctgct gctgcgccag    900
cgcctgtaag gcatcgttgg ggttcatgcc ctcggtcgaa tccaggacgt gcgtagcctc    960
ctgggacagg tacttgcgga actcctcggg agtcatctcc cggcccttgt tggcgatgaa   1020
tcgctgcatc ttcaggctga agtccgcctg ggcgatacgg tagtcctgct tacgccaacc   1080
acccttcacg aatggtttgg ccagtacgtt gctgtctact gctcctcag cctgccggc    1140 catacgggca cgctcaccgc gcagaacttc ctgctgcacg ttgtgctcga accatttgcc   1200
agcgatctgc tgaccggcac ccaggatgcc gtcgagaatc tgcgagccta cgctcggacc   1260
gctgtagttg acctcggagt cgcgcactcc gcgccgagca ctctggcccg gctggagttg   1320
cgtctgtccg acgttgatcc caagctcttg ggaagcacgt tgcgattccg ccatcagttg   1380
cctcctttag gcgtggcgcc gaacttgaag tattgacttg cgtacaggga acccgccgac   1440
atcagaccgg ccaccagcgg ggaccgttgc cccgccgtgg tactcttctg acccagcagg   1500
ccggccttag cctgagcctg gatggagtgc gcctgctcgg cgaggttcca catctgattg   1560
tccaggttgt cgtcaatctg gatcagggcc tcgccgacct cccgctcgat atccagggcc   1620
accgcatcga cggatgcacc cttgacgccg aacgccccgg cctgagcctc ggcgcttccg   1680
ccggctagca tcccctggcg cttggcctcc acctgcgagg ccacggcttg cttgcggtag   1740
ctagcggcca tgactccgag gttggcgata tcgcgggcag cggcgcccag gttgtcgagg   1800
tccgtcttca gtcgagcctt gttctcggcc ttgatcttgt tgcgctcttc cttgttggcc   1860
aatccctgtt gaagggcgga catgccgcca gcggccaata gtggtagcca gaaagccatc   1920 acacctcct gtaggtttgg ttggacttga agttgtactc gacagcccga acgttcatgt   1980
cgtacggact gtgacagctc agctcgaact tggacgtggc catatcgacc cgtgccggca   2040
gcggcaccac agcgctatcc accagaggct ccccggcatt gagttgccgg ctgaacaacc   2100 gaagggcgt tgtgtcgtac cacggctggt tgggtcgagc cgtgtcgctg atgcgccaca   2160
ggaactcgcc ggtccagccg aagtttacgt tgtaccgatg aagcactgca cgggtcgagg   2220
tcatgggcag tccgttgtgg tcccggagaa ccggcggagt gaactccacc ttcgaccaga   2280
actcgcagcc gaccacatac accgccccaa ccacggcctc gggcacgtcg aggaacacct   2340
tcgtactcgt ctcgcgtttc acgccgagat gggtacgctc catgtaggcg ccggccacag   2400
gctgtagctg gtacacggca gaggcatcct tgatcaggtc ccaatgctgc ttggtcagct   2460
ccagctcacc atcgacggtc gcctcgatac gccgccagta gtcgtattta gggtattgca   2520
gaccctcacg ggctggcagg ctgttcaggt gcatacgtcc cagggcgatc tcctggccct   2580
tctgaatcag gaccatcagg ttgtcgccag tgaagtaggc gccgatgatc tgatgtcgca   2640
acgtccagcg atgaaacgcg ttctgcactt tctcgttgcc ctgccagagg tactggtggc   2700
agatcatctc gtccgccgtg ctggtgccga acaccaggta gccgctggag gccgccgcct   2760
ggatgtactc agcaggcccc ggcatgtagc tcgggatgtg gctggtaacg tcttcggcga   2820
cgtagtggct gtccgtggac ggcgacgggg ccatctcatg caggcccatg aaacccaggg   2880
```

```
cacgctccgc agcgaagtat acactgcggc cagtcacggc aggtgccgcc ctggtatcga    2940
ggtcatactg cgtggtgatg ctgataaccg ccgtccgggg agttacaatg ccgccaccgg    3000
ggaccacggc ctgatacttc ttggcgaaga cgatcaagtc cttgttgaag gtgaccgcgt    3060
gctcgtacgg ctcagtcagg ctcccctggg ctgcgatctc gataggatcg tcgtcgttca    3120
gcgcggctgc cgacttcttg aaccagcggt gcggattgtt actggccgac atgcagacgt    3180
actcctgcga caggaggacg aggcgaccct ggaaggtcgt catgccggtg atgcctcggg    3240
tgacgaagtt gaacgtgggg ttcgtatcct cgtcgccgga gccacgtcga tcatactcca    3300
actcgttcaa gctgtaggtg tcggtaacct catcccagcg cagggccagt ggcatcttct    3360
tcaggaccca atcggtgccg taggcggccc gctctgccca gcggcggtta gcggaatccc    3420
actcgaagta taccgggggcc ttggtggagc cggtggccat gacagcgccg tccatgaact    3480 gcaccccccac accaggggcg ccaactcccg gcagcaaggc cggcaggtcc gccgtagcat    3540
tgaggctcat accacctgac gcgatgccgt agttgttgcc catatccgtg gacacttcaa    3600
cgtggatatc ggcgtcgcca cggaatgcga tgtacccgtc ctgcacgccc cgttggttga    3660
ggtagccggc tatggttgcc gcgttggcgt ccgggtctac cttcgggtac ttcttcgtcg    3720
agttgggcag agtgtactcc ggcgcaccga agaacttgcc gtagagctgc caagcgatgt    3780
agcccacgct cgtttggaac ggtgcctcag cgaggttggg gttcgtgctg gcgttgtccg    3840
gtgtcacgta ggtggccgtg tgactgtagg tggtgcccgt ggcgttgtcc ttgaccttga    3900
tggtcaggga gaatgccttc gaatactgcc ctgccttgat gtacagccag ccagtcttgt    3960
tggggtccac acccttgaca tcggtgcggt cggcttcagg cttcacgctc aggttggcga    4020
tgaacaggtc gtcagccacc gtagcggccc gtagctgcct gtaatcgtcg gccttgaggt    4080
agtcatgcac caggggctga cccatcagca ggcgaccgtc ccgctcgtcg aacaggtaca    4140
gctcaccacg gtgctgcgcc accagcatcg caatgctgcg gccaccgagg ttcgtgtggt    4200
agaggaacgg cctcggccag ggctggtcgg tatgcagcag gtgggccatc agctcgatac    4260
cgctgcgccg ccgaagtcct gacacgggat cggataccat gttgatctgc tcgctgagct    4320
ggcccggcag gcgctcgaag ggcacctgct ggctcacacc catcagcaga ttgggatacg    4380
cggattgctt gtagctcatg ctcaggtcct caagctgcgc cgccaccggc tgaagctacg    4440
cttggcctgg gtgttcagcg gacgtgatcg ggtgtgcatg cgggacagtt cgttctgata    4500
cgcctgcaat tcctgggcga tgacctgggc ggtctcgtcc ggtccaatct cgtgggtgta    4560
taccgcgagc gcagcctggt gcgcaatgac gcgctgtgcg atctccggga tacggtccca    4620
ctcccgagac agcaccaatc ggccctcgac cgacttaccg atgcggtcgt cgccggtgtt    4680
ggcatctcgc actcccaggc cgtcccactg gaggtccggg gaatccgggt agaatgccaa    4740
ggtgcccttg ggcaggttga tgcggcccgt gggatcaggt gtcagcttgt gcttccacca    4800
ggtgttgaac caccagcctt gggtcagcaa ctggatgcgt tgatcttcca gctccgggag    4860
ggcgatggcc atggttggat acgtctcatc catgctcggg attggcagct cgccgatctt    4920
gcgcaggatg acattcactg cgtcgagtag tagcataggg tttctcctaa agcgcaaaaa    4980
cccacgcagg gaatcgcgc gggtcgttag gctttgaaga aacccacac cgaagtgcgg    5040 ggtttcgtgg catcacgcgg tgatgtcgaa ggcgccgata cccttcagtt cgatggcacc    5100
agcggtgtcc ggacgacggg caccgatgtt gtacatctgg aaggtatcca ggacccacga    5160
gaatttctcg ttgtcttccc acagcttggc ctggaccggc gccacttggg cggtgatcag    5220
ggtcttgctc gggaggaaca gggcgatctg gcgctcggac tcctcggcgc tcacgttgaa    5280
```

```
gtgacggccc agcgggtggg ctgcgattgc cttggtggcg aagcgcggag tctccagcac    5340
cttgacgccg ttgaggatgg ccacgcggga cttcacgtag tcgttggtcg cgccggttgc    5400
ctggtactcg acgttcatca acttgtcgtg ctccagcagc aggctgaaca cacgcggcga    5460
catcggggtc aggccctcgg agtagaccgc atcgcccagg tcgcggtcga tgaaggtctc    5520
gactacgcgg cggtgcatgc ggacgatctt gtcggcagcc tgcttggcgg tcaggccggt    5580
caggtccagt ttctccagca cgcccggcga gaacgcatct tccaggtcca ccggcgcgtc    5640
catcgcggca gccttgatca cctggatcag gcaggcttgg tcgaacttgc gagccagttc    5700
ctggccgtcc agctcggcga cttccttgcg catgtcgaag gattgggtcc actcgtcctg    5760
gtggtcgaac tggtggcgga ggtacagcag ggtgtcgacg tcaggttcc  acttgtcgtt    5820 cacgactcgg ctgcgctcca gctcttcacc ggcgcggcgg cccttggcct cgacgttacc    5880
caggcgatcc aggcggacca cgttcgagcc acgcaggtcg cggatgttca tcagcggtgc    5940
gaacttggag gtgtaagcga agtgcttatc gacgatgccg aggtgctctt ccaggtggat    6000
gtcaacgtcc gcgttcttgc cagcgtagtt cggacgagtc aggtcgttca gaaagctcat    6060
gcgattctct ctcttttgga tgtgggttta aggccgagt  agggcagggt cgttagatac    6120
cctgcgccat gcctgcctta cgacgctcgc gcagcgcagc catctcggct tcggatgcgt    6180
tcagcggcag cttagatact tccaagcggt actgctcagc gctcagagct gccagtgcag    6240
gtgccgcagc acccaggggt tggccggtag cctgtaccac ggcacccgag ccttgtgcga    6300
aggccacaat ttgcttcgct gcgtactgca tggcctgggc atcgcccgag tccatcagcc    6360
gaccgatggc ggccttggtg gccgggtcag cgtgttggtt gaagacgccg gcagcctgct    6420
tcaggatggc ctcaccgccg acggcggcat aggtctggct caggacggcc ttggtctgcg    6480
catcaacata ggtcaggacg cccttggcca cgttgatgac gtgctgcgcc tgggccgggc    6540
cgagaacttc cttcagatag tgctcgtcga tgaaccgagg atcgcggttc tcggcggcct    6600
tgccgaaggc tcggacggta ccagtttgt  cagagaacgc ctccagatag ctgatggagg    6660
gcgccaactg cggatcgcct tcgaggttcc ctgccaaggt gcccacgatc tccccgttgg    6720
gagtgaaggc cggcggcggc gggacttcca ggttctcggg aagaactgca cccgcagccg    6780
gcggagctac cggggccggc tgagcgggtg cttgcggaac aacgggttga cccacggcag    6840
gtgccgctac cggctggtag tgcggcgtca tggcgctggt cggaacgggt tgcggctgct    6900
gggtcgggat ggccagttgc tgcggcgcac ctacctggcc gggctggacc ggagcctgcg    6960
gctggatcac cgggttcggc atcacctgca catgactcgg tgtcggcgcg gcggcgggcg    7020
gtacgttggc aaccaggtta gcgaggcccg gcggcagttg ctgttcgttc tgttgggtca    7080
tctatcagac tcctgcgagt gcattggtca tgtcggaagc gccttccagc aaggtctcct    7140
gcgcggcttg ggcctgcgcg gcctgctggc gctgctgttc tgcctcggct tccagttcgt    7200
cagcgctctt gtagaactgc gaggtatcga cgctgaaggc tgcccaaatc gtgtccatca    7260
tcttcggtag cgagatgcgt ggatcgagct gagcaatcgg ggccaagcca gcaatgacct    7320
gggaagcgtt gagcatgctc tgcacagcgg cggagcggga cagggcggga aggcccgtct    7380
cgatagccgc cttgtgctgc ttggtgatca agccctggag tagcgcatcg tccacctcag    7440
acaggcagac gtaggccagg ggcgactgaa ggttctcggc caggagcgaa tatgtgccgc    7500
ccagcgtgtt ctccgcctcc tccgcagtga tgcggacttc ctcggcggtg acgcgctcgg    7560
cgtcgcgctg gttggcacca tacatgaacg cctggttcag gcggacgact acggcttgca    7620
```

-continued

```
agctctgctg gatagcggcc atcttgttgt agtcgccacg ctcgtacgca cggacggctt    7680
ccgcaccacc tggcacgtaa tcgcccatct cggcgtcttg gtagtcatca actaccgcac    7740
ccttggcctc gtccacgagg ttcaggacct ccagcgactc cagctcgtac aggccgagtt    7800
tctcactcag cagggacagc ttggcgaagt cgccgatgta gtcctcgacg tggcctcgac    7860
cgtagtgctc gccagggggcg aggttccagg tcggcacgat gtacgggcac aggtggatag    7920
gccagcggcc ctccttgccc acacgcacgc cgtcgatctc gtggtacagc tcggcgtatt    7980
ccatcgccgt gcccttctta cgctgtacgt gggtgtacaa gtccacgctg cccgaaccgg    8040
acaggttgcg gcctgcacgc atcaggtcct gcttgtactc ttcgtccagg tccttggact    8100
tgtagcgctg ctttaggacg atatccatcc accggccagt cgcatctcgg cgcaccgcgt    8160
aagagcggag cgaccatgca accaccgtag cggcgtcgct gtctcggtac agcagagcat    8220
tgccagtcac gatcagtagc ttgatcacct gcgtcaggac cgccagggag gcgttctgga    8280
acaggcgctg tgttgctttg cgatccaccc gagccaaggc agcggtcact tcggtaatgt    8340
ctgtgtcccg gctgtcggcc tcgcggcgga tcgcatcagt gagttcggat cggaagaacg    8400
gaatccccgt ggggaacagc gatctcgcca gcttggcggc gaggttgttc accaggaggg    8460
caccggcgga ctgaaagtca tgctctacga ctccccggct gccggacatg ggatcgacca    8520
tcaggtaggg aagcgtggtc ttggcgaact cgatggctcg actctccacg ctcccatccc    8580
gaagtttctc ccacagcata gctgcggtgg ttttcatggc gtacctcgtc agtagttgat    8640
accgagggtt tgcgatacgc ctgtgcccgc ctgattccgg cgccgtcgcg tgccggtgcc    8700
agtggcatcg gccatcgctc ctaggtcaac ctgcgccacg ttctcggcgg tgaggtcaac    8760
ctgctggttt cgtgcgagct ggtccgcctg ctgctgcatc aggcggttct gctcttccat    8820
cttgcgggca tcgattgtg cgccgctaag gtcggtgcct agcaggccat cagcgagttt    8880
gccgatgatg gtcttgccta gcaccttctt gactttcttg cccataaggc ttggctctcc    8940
ggtagtggat cgtgtaccgg ctatcgcttt cacgatggct ccagcacacg agggggattt    9000
gaccccagcc ggcctgacgg tggagttcgc ggatgaactc ccggaccacg cctgtattgc    9060
ggtagcgcgg taggacgtac tgccactgtg ctgtgacgca cgggccgacg tggggatcgt    9120
cctcgaacac aatgcaggca ccgccggcca actggccatc gcggaatacc aacagctcgg    9180
ttcgatcgtt gccctcgata ctgtccagca tcgcattcag ggcgtcgtct ttcgagcgga    9240
agagggtgaa ttcttccaac tcctgtattg ccagccagca cagcccctgg agttccgagg    9300
gagtgccggc ctttgcgtgg actcgccaga tggacttgtt catcacttca actccactgc    9360
gatggcatcg cgtcggcgca ggcgtactgc tcgcaccacg tctcgcctac cggcctggaa    9420
ctggatgtct tccatcgtgg ttccaggacc gatctgatgt tcggggaagg tctgctctaa    9480
ccactcgatc tgctgagagg tgaacgtgac aggacgggcc gtaccttgc ctgttctcga    9540
tccttccact gtgggtgaca taaccatagg tcggtgggtc ttcatagtag ccatctatca    9600
tatctcctat gctggttagt ctattctatc tagaatcctt cgtagtcatc tagtctcatc    9660
ttctactcta cctctactct tcttctaccc tctggtcttc cctgacctct ctcttcctgc    9720
tccctctac gagggccttg gacggatgca cttgctccta tgtgggtgac ataatccct     9780
cagcagaaga acgcccagga gtcccgtaca gcctccagat tcaacgatcc tctccgggggc    9840
ggggtagcct ctatcccgag ctgttttgcc agttctacga gcacacaggg gccgctgtac    9900
atggcgatga actgctccct gatgtggacg tgcatccgat ccacgtctgc cgcataggtg    9960
cccatgctgt cgtggatggc ctggatcggg atacctctg ccgcacaggc cagggccgtc    10020
```

```
aggcccaggt ggctgctgtc cagcccgtgg acgaagttcg gagcgatgcc gttggcgttg    10080
cgtaccgggt ccagctcgtc cttggcctcg tacagggtga cgtactcgac agcctcggcc    10140
cgcagcctca cccgcacctc ctcggtcttc gggtacgact ggaacacctg catgccgagt    10200
ggcgtgatcc agtgcaaatc cttggatgcg tcaggaaggg ccttagcgag ccgctggagc    10260
cattccatgg cgaagactgc cgatggtact gtctcgcgaa ttgcgtccag tatgagcgtt    10320
gccatgtagc ttcccaggcg gtatgacggg atacctcgg gaatctccag gccggactcg    10380
tccaggtagt ccaggcagtg gtctaccacg cccttgaacg tggtgccgta taccagcgtc    10440
atgcagggct tcttcgtcag gcttcggat agaccagcct tatcccacaa tacagcgtag    10500
ccccgagcct cgccttcagc actttctctg tctcgtgcca gagactctgc aacgagaccg    10560
agaactcggg agtagatgtc agctttggca agtccaggtg gcagcaggtt gacataggct    10620
ccgccgatct cgtctcggag aatggctgag tagtgctgga ggccggagca ggttgcatcc    10680
atgtggacga tgaacccact tcggtaagcc tccggctggc ctgatgcgta ggccgcccgc    10740
agctccagca gacctgcgat ggcgcacagg ggcgactcgt cttccgggaa gagactcgga    10800
tagttctccg ggccttcgtc gagtgctcgc tggaagtcgt cccatcgctc atcgacccag    10860
gctgcccggt cgtcgaagta caccttgtca catccgaggg agttggcgac gtggaccttg    10920
agccagtaca ggccgcgctt accgagggca cgcttttcgt ggaatcgcag acacgccttg    10980
gcgatgtcgg acccctgggg attcggtgtg ccccaatagt acatgcggcc acgggagtca    11040
acgtgcatcg ggaagtacac tgccttgcca tgatgctctc gaacaactcg gtagagtgca    11100
gcaaactcgc gaagcttggc ggtatgctcc cgctcgccgg tgtaccatcg gtggacggat    11160
cgcttccagc ggttgaaggc ttccagctct tgttcactgg cgttctcctt ggcccactcg    11220
tcgccgagcg ggaactcagg tttgtccggg taggtgcgct gagggatgcc cagcacaccg    11280
ccaccggaag tgaagacgcg ctcgatgatc tcgtacacgt cgtggttgat ctcgtaggcc    11340
actgattgca gcgcgttgac cgcctcatac accctgggca tcttgtcccg gcccaggtgg    11400
cgtagctgca tctggcgcgc ccgcttggtc tggtgcttgg tacggcgcac tagcacatgg    11460
tgcttctgcg ccttagcgct gtagtaaccg ccatcgcacc agtcgttcca cggtcgcggc    11520
ggtgccagca tcacgctacg gccggggccc cccaggtca tcgccgccga agggtcttgc    11580
aggaactccc tggcttccgg cgacggctcc aggtggacgc tcgtaccgcc ccgacctgtg    11640
aagcggttcg gctcgaacag gccgcactgt atcagcggat caccaatgaa cttgccgagg    11700
cgcaggtagt cgccatcctg caggtcgata cgtgcctctt ccggcagtac cgcgtccaga    11760
agggcgtcca tcgtcttctg gatgtgccgg acgctgcgag tcctgctggt cttgaggtag    11820
tccagcgtcc ggtcgtaata gggttggttg accttgaagg ccaaccgcac ttcgatctcg    11880
cgacagagca tcttacccat gtgggtgtaa tacttcgtcg ctgtgatcgt tgggtagttg    11940
atgagcatcg acagcccagc ccgcagcgcc atgaccgcga ggtcctgggc gtcgatgatc    12000
cgcagcaggt gccggagctt cgctgccggc cccgccgcct tcgcttcctg gtgggcgaag    12060
atcgcttcgg tcacgatggg gagcatccgc atcaacatga tgcgcgccct cgggatgcgg    12120
tcgatggacc cttgggcaat cgccttttcc aaggcaatgc gggcgtcatt ctgcgccgcc    12180
ccgaccaggg cctcttcgtg ggcgatctgc tgctgtatca ggtccattcc gtctcctatc    12240
gtctttcgat tacgcgcccg atatcctcgg gaccccactc ggcctcggcc aggctaaccg    12300
ccccatccag cgtcatcgct cggtagtcac gccattcccc gcagctcaga atctcagcgc    12360
```

```
ggaaccagcg cagttccacc agcttcactt cccgctccag gcgctccgcc atctcccgta   12420
gaatgtcggg aagtatgaca tcgcccagt  cccgatggct gaccatcgcc ggcgtgatgt   12480
acgctgtgac gtagttgacc ccgatgcccc gctcgttgaa ggcccagatg acccgaacac   12540
cttcatcggt ctcgtgcggt cgggtacacc aacagatttt actcattgcc tttctcccga   12600
tccatcaggg ccacctcggc ggcagccatt gcgttgaatg cctcatgcac gaggtgcatc   12660
aggcccgact cgtcatccag cggcccgtcc agtaggcgct tggactcgtg ccgatgctgt   12720
gcggccttga actcgccaac cgacatcttc ttccagtcgt gcggcttgta gcccttgacc   12780
tcggcggccc actgcatcat gcgggcaagc tcccgcttga gcagcgggaa gccatcgacc   12840
accaggtgca tcgggagctt gccgaccttg cgttcgtcca gggcggcgcc cttcttgtag   12900
cgctcacgtt cggtcagcgc gatcccatac gacttgtcga cgatcatggt gtctcctcag   12960
ttgctcagca gggccttgcg ctgttccgag gtgttgcggg tgtaccgccc tcggctccag   13020
ccaccacagc caccgcagtg atagtgctcg tacttgccgg tctgcgtatg cacccagcct   13080
tcttgcttaa catccgtgtc gccgcacttc gggcagcgga tggtcggctc ggcgtcattg   13140
aagtacacgg ccacgttggg atggccgacg aaccacgggc gcatcaggat gtacagctcc   13200
tccatcgatc gtacgtcgtc gatgttgtac aggcgcatct cctcccaggc ttccgggttg   13260
tcctgtaggc aggccgccca caggtcgaag ccggggaact tgccgtgaag gcgcttcttg   13320
atggtgcatg ccttgtgggt catgtactcc agcttgcggc tggtgaacgc gaattgctgc   13380
ttggcgatga tcaaggtgtc gatcaccttg aacggtctcg gcggcggcat cttgttcagg   13440
aagaaccggg cgttgatctt gggcacgtcg aagcgcttgc cgttctggac tatgatgatg   13500
tcggcctcgt ccagcagctt atgcagggcg accagcaggt gcatgtcgtc caggggtca   13560 ccctggcagt ccatgtagat cacctcgtcg ctgtgcatcc acttcgcaca gaacgacagg   13620
atggtccagt cccgcttgat ctggttgagg cccacgttct gcttccagag cgaccagacc   13680
cagccctcga taggcgaggt ctcgatgtcc aggctcagca ccttcggacc ctggcctacc   13740
acgttgccca cggcgccagg gaacttgcgc actacctcgg cagccttgcg gcccagccag   13800
tgcatcgcgc ccttcttggc gtacatgccg cgcgtcctgc tgtcgtggaa gcccagcttg   13860
atgcaccagt tgcggaagca ctggcggctc acctcaccga agcgcgaatg ctcggtcagg   13920
tgctcggcac ccttcttgag gcccagctcg acatagacgt ttcgcaggta ctcattggtg   13980
aattgcttgc ggagtttgct catacgttcc tcgcgttgtg ctttgcgacg gccatcgccg   14040
ccttgcgttt ggcggctgcc tgccggcgct tggccagctt cgcttcgtgt ttctcctcgt   14100
cggtcttgtg caggggtag  atcagcggat gcttcggccc ctccagatac gtcaggaggg   14160
cacgaaggta ggggatgatg tcggaatact tcatcgactt gcatcccag  gaacctgccg   14220 cattcgttat cttgccttct gcggtgttac aggaccggtg caggacgccc cgcaccagcc   14280
ccgtttcgtg gtcgtggtcc atcaccgctt cgcccttcac gctgatatcg atgggcttgc   14340
cgcagagcgg gcacagcttg ttctgctcgg cccatagctt cagggtgaag gtgcgctgtt   14400
gactgcgcgg tatctggtag accttcggct cactcgtcat aatcgctctc cctccgcttc   14460
tggagcagcg cctcgtggta ggcgtccagc tcgatgatcc actggcggaa ggccggacga   14520
aggtcgcggc ttaacaggta ctgcgctgcg ttgtcggtag gcgttcggcg catccacagc   14580
acctcggcct ctgccagcgg gttttgcttg atcttggcgt acgcctccag gatcatgtcg   14640
atggcctcgt cctcatccgt gatcggatgg aggatgtcga aggccgtctt catacccgcag  14700 agcttaccgt tgaatcgatc gatccctcgg atgttgtcag cggtgtcgcc gccgagccac   14760
```

```
tgcgccaaga agaacttccg tccatggccc ttgagcttga actggccgga aggcgtgtac   14820
gcttccttga ggtagccgaa gccgccttcg attctgctca cacacgccgt atcgatctcc   14880
caatacgggt agatcgtcat ccgcaggtct ttgtcgtcgg accggatgat ggccttgtcc   14940
tgcatggcgt aggcgtccat catcatgccg tcgtccgcct cgaagaacgt gtgcaggatg   15000
acatcgatcc cctccggcgc ccctcctcgc tcatgcacgt ccgccacggc ccgccgcagt   15060
ggctccagca gcgcgggctt tgccttgccc ttgcgctggc cctggtacgg tttcatggtc   15120
ggatacgtgt cgcggtacgc cttcgcccca cctgctgccg tgaggtgaac ccgtgtccct   15180
gtgcagtgcg ctaggaactg ctgctccaaa atgagcttcc agaatcttcg gagtgcagtg   15240
tccagggtct tagcagtggc cgcagccacg taggcgggtc cgtcggcgtc acacaccaac   15300
gtcccgcctg ccatgctgcg gtcgaactgc gcggatagtc ctgccaggaa ctcttccgat   15360
ggcaggcgca ttagacctgc ggtactgccg gcactaccgg gaccgccggg acttcgaccg   15420
ctgccggagc cgccgtctga gccacctggg gcacgtcagg cagcacgttc tgtgcctcgg   15480
cagtacctac cacaggggcg gccacattcg ccacctgggg aacgctgggg gccgtctgag   15540
ccactgcctg gggaacagcc gggacagccg gtgctgccgc tacgcggcg tcggcggcca   15600
cgttgggcac tgccggcagg ttgctgcctg cggcctgggt cgtcggcttg atgatcagat   15660
cgtcgccgcc gcccaacatg atgtgcaggg ccgagccggg gaagttggtg gccgagcgaa   15720
tggtctcttg caggaagttc ttggacttgc cgttgtccga ggtgccttcg atgaacaggg   15780
cgtcccaggt ctccttggtc ggcgcgtcga agaagaagta ttgcagcagg tccagcggca   15840
gttccggcac gttatacggg ctgccatcga ccgggttata gggcttcatg atgccgcccc   15900
aatcgatgtc gttgcgttcc ttaccggcgt tgttgccctt ggtgatcttg gtgcgcttga   15960
tcgggatgat gaacgcctgg ccgagcatct gagcgaagtg ggtatgctgc ccgctccagt   16020
tcatcttgtc gaaggccagc ttggtcttgg acttttcgtt gttgccgagg gtcatctcga   16080
aggtacggaa caggccgggc ttgatcgagc cgtcggcctc gtaggtgtgg aacaggtcgt   16140
ccgggcggct ctgcgggtta ccggcctgcg ggttcacgtc gccccacagt gcgaagccca   16200
ggcggatttg cggcgccgga ttcttgagct tgccctggaa ttccttggcg tggtcaccca   16260
gctcgatgta gatgcagaac cggcccatgg cggtgcctgc cgggaagatg cgaccgccgc   16320
caccgccggt agaggtttcg gacatgtcga tggttgcggt ctcggcagcc ttgttggcca   16380
gggcgagggc ggcttgcaga gcgttgagtt gctgagtcat acgtggtctc tcttgtgtcg   16440
aaggaagatt taaggccgga gtagggaagg gtcgtcaggc gttcgaggcg tgcggcagcg   16500
ccttgaagac gatggacaca ctgcgcctgg acgcaggccg gacgaggacg ttcctgtacc   16560
ccagggcctc caggatggtt tcgatgcggt ctaccaaggc cgccgcgctc ccgccgtggt   16620
ggtcgtcgaa tgtcatcgtc ttacgtgggt gggcgagggc cattccgatg gcttgcatgg   16680
cgatacccgt ggtgcggcca gtacgccgct cgccgggcag gcatccggtc tggtccagga   16740
atgtcttgac gaactcgggc gtgtgcagcg gatgcagttc tttcactgaa tcacctccat   16800
attgaacatg ttcggcccca tctcagccac tgccggaaac ggaacgtctg cgatgtcgta   16860
gcccaggcgc tcgctcatgt agcgggcagc gtcggccatg atgtcgcgca cgccttgtt   16920
gacctcggcg gcggtgtcct tgtggcagtc ggtgtacacg gcatcgtgta cgttgttgat   16980
caggaactcg gtgaccatga atcctgggcg atgcagcatc caacggaaga tgcgccccac   17040
gctcacggtc atcatgaacc cagcctcgcc ctggttccag tagttggcga tctgcgtgtc   17100
```

```
cttgaagtcc atgaccgtct tgcgctgttc cttgtcccag cgctcctgtt ggcggaagct   17160
gtagcaggtg ccacccggcg cttgccagaa tcctcggcgg tactggcgcc agttgccatc   17220 cggcccatc tcgctgaagg cgcctgccgg catctggtcc tcggccttgt acatgacgag    17280
gctggtggcc tctgcactgt cgcggacgat ctgccggaat gcgatggact cggggaacag   17340
ggccgcctcg ttgtccagga attcctgggc ctcttccacg gtacagccgg tgttgaatgc   17400
gataccagcc gcactcgcgc catactgcgc cgagaatgcc ttgggcttga tgttctttcg   17460
agcctgcatc atgcgaccgt gccacgggtg gttggggtcc ttcttgatgg ccacgagctg   17520
gtcgtagtcg aacccgttcc agttgttgtg cttccctgcc aggcggtaca agtgcatatc   17580
agtgccggcc atcagtttcg ccaggaggtt ccgatccttc gacagggccg ccaacatcac   17640
cacctccagg gcggtatagt cggtctcgcc gatcatcccg tccgcgccga agcgagacac   17700
gaacatctcc ttcacgcggc tgccggcttc cgggtcgtcc tcgtccttcg acgggagctg   17760
ctggaggttc gggcggctgg acgacagacg cgttgtcgcc gtcgccgtcg tattcagcga   17820
atggtggatg atgccgtcgt cgtccacgta ctggagcatc cccttcgtgt ccttaatcgt   17880
cccatccttg ttgtaggtgt gggtgatgta aacgaggag ttgtccttgt gcagctcggc    17940
caggcgcatc aacagcttgg ccgcctcgaa gccctgtttc tccagagcct tgaggcgtc    18000 gccgctggtg ctgaacacgg gcgacccatc cgccagggtg agggcgcact ggaactccgg   18060
gcgtttgccc aggaatttct cacgcactac ttccggaagg ttggtcaggt tgatcaggcc   18120
ggggaaccgg aatcgctggt catcatccca cttggtcgcc gggatgtccg tatcctcccg   18180
gaacaccttg acgctgccct tgttcttgcc agcggagaac gtgatgaccg ggccgtgctt   18240
ggtcgccagc tcggtgatgg tgggccagtg ccactcaccc tggtcggtca cttcgtggat   18300 cgggaccgc actgaggtac tctcgattgg agtccccgc ttggccgtac cgaagcgcac     18360
gaagtcggct ttctccatcc ggccatcttc gtacggcacc cggcccttgt accgcacctc   18420
gccaccgtag agccatgcgc tcatatggta gaggctggta tacttgaact cgaagtattc   18480
cgggaagtcg ggcatcagct tcttcagctc ggcctcgatc ccggccacct cttccagttg   18540
cttggcgtgt tcaccttgg cgacttcgag gtccaccttc aggccggcac actccatcgc    18600
cgagaaaccg atcagggcct cgcagcgctc caggtagcca gcccacatgc cacgggcctg   18660
aagcttcatc aactgccgt agaacacgag ggcggtattc tcgatgtcgc cgcacgggcc     18720
ggacaggtac tcgctcagca ggtcctggtc catctccgag gtgagcacac cctggtccca   18780
cagcatcttg atgccgtcca ccttgtgggt gccgccgtac ttcggagcca gctcgtcgag   18840
cgccgggtac agccacgtct ggtgactcag cagatactcg gcttgctggg tacaccagac   18900
ccggccaccg cgtcgcaaga aggccaggta ctcgtcccgg tagcgggtga agaaccagtt   18960
cgattcgaac atggcgttgt gagctacgat cacgtccacg ccgtcgaggt tgaaccagcg   19020
gttgttcggg tcctcggctt cggccctgct gcggaagcga tgctccacct tctgccgac    19080 cttgccgtca acatcgtcac gccatccggc catgacgatg taattgcggg ggtcaaaggg   19140
cgacgccttg cgccccttgt gctcgtagct ctcggtttcg aggtcgagga ttcgtatcgt   19200
cgtcataggg tataccagtt cttggtgacg aattcctggg ccttcttgag catccttcc    19260 agcacctgcc gtgggactac ctccatcagg tacttgatga tgctctctcg gtcggtgacc   19320
agcacgtact cgggcacaga ctggacgtag cggaggtgcc ccagcttagg gtggatgtag   19380
tccacctgga ggcgcagttc ccactggcct aggatgccta ggtattcctc gtccaccttc   19440
acctgaattc cagggaacag cagattcagg ggaccgtgta tgtcctggag taagcagcgt   19500
```

```
aggacgcgct cgtgttcagt tggtacccgc acggcgttta gcctcctgtc gcatcatccg   19560
gtggagtcgg cggcgagctg cacccaggga cgggcacaga tacgcatttc cctggcagtg   19620
agccatgaac ccgccggtgt ggtatttgaa gacggcacct ccgaagaacg tgctccaggc   19680
attcgccggc atgggcgccc cgcgtttaac ggggcgggcc atcgcgtggt acagcatatc   19740
gtcaccgaag aaacagctcc ggtgggttcg aataactctc ataccttgtc ccccttatag   19800
ggcagaatgt cgcggaagcg actgaacttc ggatggcgca gggtgtgcgc cgagcgctcc   19860
atcgcagtga cctcgaccac acggcccagg tctggcatat cagggtggtc ggccccgccc   19920
agcagttcgg cctcggcagt cagcagggcg atccggtctc gggtcaggcc cgtagccgac   19980
acgattccgg tgccgtcttc gaggtctacc ttgtagccga ccaccttacc gacgttcgcc   20040
ccggtcttgc ccatgacgaa gcccacgacg cggccctcga cggcaatgct cggcttcatc   20100
ttccagcaac cggagacttt gccgttgcgg tagggcaggc tcgggtcctt gaccatggcg   20160
ccctcgaagc ccatgctgcg gtactgctgg tagatgtgct cgacctcttc caggcaagtc   20220
gcagtgcggt tgttgatcag gaacaacggc ccggtagctg cgcccagggc agtgcctgcc   20280
agggcacggc gctctgcgtt gtccatgtgg gacttgcgct tacgcagcag cacatccaca   20340
tgggttgcgt cgaacactgc gaaccgcagg ttggcgtact cgctggcgct cagcggctcc   20400
ttcgactgga gacgcccgca ggactcttcg aaggtcatgc cggtcaggta catctcggta   20460
tccaggacga tcccggcctg aatgacgtgg tggtttaggt ggttgacgat cttgtcgtcc   20520
aggccggtca gcgcagggaa cgcccgaccc gagcgggata cgatcccgtg ctcacccacg   20580
atggcacgac agccgtcgat cttcggttcg acggtgacga agccgtgctt cttaccggcc   20640
ttctcgatgg cggcggggtt gttgtccacg ccgcgccata cgcccttctc gatatccagg   20700
atcacgtcac gcttggtgct cattacttgt tctcccatcc gtaatacgcg gccttggccc   20760
gcatcttctc gcagcgctcc ggtagacgtg agccggcacc gacttccttg ttcacgcccc   20820
agttaacgtc cttgtgcagg tacgcaccca gtcgcggccc gccttcgggg tccggccagt   20880
tgtacgcgat gcccacttgg ttgatggtga agtcgaacga ctccatcacc cgaccgaggc   20940
tgccggcgtc atagtagtta aagtccaagt ccatgccacc caacccacgg cagcccacga   21000
gggacatcac gcccttgaag ataccgccat cgccgccatc ggcgtagtcc gagcgccagc   21060
caccgtcccg gacgaagata gggtccagga ccgggagtgc cttctggatc aggtgctctg   21120
cacgccccca ggtcatgcta tacagggcaa catccacgtc cttgggagtg gcgccgtgca   21180
tcaagtcgcg agggaaccca ccggccaagg cgacgccctc ctcgtgagtc gcgtcggagt   21240
acaggcacaa cagcaggccc gcgacgctgc ctagtaacag ctcgatgcca cctatcggaa   21300
tttctttggt gccttcgagc acccggctat gcttagcttg catgatctac actctcaaag   21360
aaacgacacc gcgcggcgtc gaagttaatc atagcctcca cgttcgaagg cttcccgtcc   21420
atctggaatt tgttcttcgg cagggacagg ccgcgcatga cctgttgatc cgcaccgttg   21480
agacggccca ggtggatttg cacgtccaca gcaccctgta ccgccgtctt cgaatccttg   21540
aggcaagact gcggtgggaa caactggtcg tgaccgtcgt tgctaatctg ccacgtcatg   21600
aagctgatga agtcgtggcg caccgccatc tcgcggacct cggccacctt gtactccatc   21660
tcgtcggtgc gattctggtc cttgcgctga ccaccttga cgtgcgccat catgtcccaa   21720
aacaccaccg ccggcttcat cgcgtcaatg acctgctcgg cttgggccag cgacccgccg   21780
tggaagtcct tgatacggat cagctcggag tcgccaccga ttttctcggc gtacatcttg   21840
```

-continued

```
cgaacctcct ccgggcccag ggcaagaatc tcgcccacgg tcatgcccaa ggctgccgag    21900
tacaggcgcg gcttgatccg ccggcccttg ccctcgttgt tcagccacag gatgggtcgc    21960
ccagggtcga agtaccgctt gagctgcggc gcgatatgga cagcgatcca ggccatgaac    22020
gaggtcttgc ccgcatcagg cggcgctgcc accaacaccg aggccccggc gtggaggccc    22080
ttcatgtacg ctggcagcac cagccccggc agcttgatgc cgtggtcacc ctgctcttcc    22140
gccaggatat caaacacgtc gtccgtcacg tagtcggtcg gcgtgctgac cccttcgcgg    22200
cgcagggcct cgtcgctcag gcgtcgcagc tcatacgcca ggtcgatgtc ttcgccctgg    22260
ttgtactgcg ccaggagggc atccaccctg cctgaaaaat ccagttcgtt gagctgggac    22320
acgacgccct gtagcgagtc cgggtctacc ggcttgtcca gttggttgac gaggttcagg    22380
actaccgcca gttgttccgg ttggtagcca cctcgcagct tgatcagctc gcgcagcgcc    22440
tgcgggtcta ccttctgatg cgctgggtag accttccagt attgctcgat ccagtcgatg    22500
acaaagcacg tctccggccc catcatccct tcgggcacca cactccgcaa cgtgcggaat    22560
cggtcccggt cactcagtgc gtgaagcgtc aatacgtcca attactaggc tcctatctg    22620 ctcgcgggtc aggtccttgg ggtcgaaccc gtccggcgtg ggtattactt ggccttcgat    22680
aagcagggac cggagccggc gcatcacgcc tgcactacca cggacacctg ccgggtcgcc    22740
atccaagaag atgaaggcgc gcttgcaggt ctgctgcaac atgatcgccg ccagcctgtc    22800
gcgcagcctt gtaccgttca gaccgacagc gaagacttcg ggacaggccc accgcacctt    22860
cagcgccgac aagtagtctt ccgtcagcac ccatggcctg cccattgata attcctgggg    22920
ccatccatgg taatccgggg caggataccc gtagcccacc cacttgggat tttggtcggc    22980
agtagcgcgc ccaatccagc ccgcatcggt agggaagata agccgatgct gcctttcgct    23040
gtacagcagc ggcagccctg gcgtcatcac gttgtagtcg ataccttggg acagcagcaa    23100
accataaagc gattgatagc agtcggcttg cgtccagtcc gaggcatcct cgggccaggg    23160
catgaagcgt tcttgatccg cgcattgtac cctccgcaca tgcgttttct cgaccacgcc    23220
accctcctga caggagtagc agtacgccac ccagcggtca ggcaggttct tgcaggtcat    23280
gttggtcccg ccccggctca tgctcttgca tcctaggacg tgtcggaacc ggcctacctg    23340
cccaaccgcc agggattgcg cttgctttag ccatgagtca cggcgcagtg ccattggtac    23400
cattcctccc acaaaggccg cagcccacct cgtgcctcga acatgtcctg gaggtgccag    23460
gtcatgcggg cgccgtaggc gggccgccgt tgttctgtgt gagcagcacg cccagggcca    23520
ccagactgaa ggcgactccg atgaccagcg gtttgttctc gataagccat gtcatcacct    23580
catacgtcat ggccgggtgc cctcatgtgc agcacgtccg gctctcctgc tgtccagttc    23640
gcctcgcggt gggtggtgct ccagcccaag tcggcgtaga acggctccag gaactcgaag    23700
caggtcagat actcggcacc cgccagctcg gcggcccgca ccagctcagc gccgatacct    23760
tgcctgctgt gccgatcatc aacgcacagg gccttcagtt caccgcccac tacgaggcag    23820
gaacctacca tcagacctga caggtcgaag gcaccgaggg ccagcacgcc tcccttcttg    23880
cgccagatgt cgctatcttg ccagccactc cggcggaggt ggagcacaca ctcggcgata    23940
ctcgcactca gctccccggc tggactcagg ctttcccgga acgggtggta cttccgctgc    24000
cagaggaacc actgccacca gttctcggcg ttgctcgggg cttggatgct gaatacgtgg    24060
atcgtcctga tttgaatcag gccgggatgc aggctcagcg gatacaggct cgtcttgctc    24120
atcttctaaa tccctcaact tgcgctggcc gaagtcaacc aggtcctgcg ccatgtaatg    24180
cacaaggctg ccggcacacg ccgccacctt gtcccaggtt gcccgcttac cgtcgatgca    24240
```

```
cgggaagaca gcctcgtcct ccagctcgac gccgaagcgg tatccgttgt aatgcgtgaa    24300
atggtagtgc atgttcgtga tcctccagac tcacacgaga gggcgctcta ggaacgccct    24360
cagatttgac cccggagtag gccctagccc gcgaagatta cgcccaggag gccgccacc    24420 gccagcccga tcatgcccgc tgcaaatgcg gcgtggtcta ccgtggcgcg tgccttccgc    24480
ttggccttgg caacccggtc gtttgccctg tccacaactc gcttagcgag ggcggcatcc    24540
gcgaattgct tcccacggat agcattctgc aatgcctcca gtcgggtagc cgggtcgtgg    24600
tccgcgaagc cgatgcccca gggcagccca gccatctggc ccacatctcg cagcttactc    24660
acggccatgg tcgcctggtg cagtcttttg gatactgctt ccaggtccgt gcgcgcacgc    24720
cgcaactgct caccacgcca cttcgcgttg tctgctatct cagccagccg ggttactcgg    24780
ctggcgaggg agccggctgg aatgccgcga cctcgcacgg ccttacgaac cgctacctgt    24840
gaattgacca tggctcgcag cgcgttatcg aagtcgctcg ccatcagagg ccgaccgaat    24900
tcccgccggc attcacgcac gcctgggaat gccttgagca gcaaggcctc gtactcgtcg    24960
gcgcgttgct tgtcgtcctt gccggtgttg tacatcgcca ggacgtgctc ttcgatcttg    25020
gtgaagttgg ccggattcgg gttgggcgtc acctcgatgt cgggcatgcc gaaggctaca    25080
cccagcgcac gatgtttgca cactttgcgc tgaggttcca cgtggtccac caccgcgtcc    25140
acgcgcacct tgccgtcctt acagcacgcc tgctcggcga ccttcacgcc cgagattcgg    25200
gcggtgtagc tacctgccag tgcccgatgc ttggccacgc ggcgcatctc cggggacacc    25260
tgggcgcacg gtacgccgaa catgctggct gccagcttgg tgaagtggtc gttgcattcc    25320
atggtcagac tcctgccagt ttcagggtta cggccagtcc tgcggtcagc aggcataccc    25380
aggccatgat ggttgccttg cgagcgcggc gctcttgtgc ctcgtgggca tcatgcgcag    25440
cgttcaggtc gttctgcaac aggcggatgg tcgcctggtg gttgcgaatc tcatcgatct    25500
cccagcgacg tgcgcgctcg gctgcctgga gacggcggct cagcaggtcg atgtcctctg    25560
cccgctgctg gcacacggcc agggcagccg ccagacgatc ctccagttcc tgggtgaccg    25620
ccggagatga gacgctgaca ctacgcacgg tgccgttgat gtgctcggga ttgcgcttgc    25680
tcatggtgac tcctcctatg gtatggctag ctcgcaatag gcccggaggg ccgggcctat    25740
tacgtgcggg ccttactcgc cctgggcgat ggcttcgtcg agggttgcag cttgggctgc    25800
cgacgactgg acgcgcgga tggcgctggc cttcacgtcc agcagcttgg ccggtgcgct    25860
gtcgctgaag cggaccagca cctgatagac gccggcgacc acactgatga cttcgccgct    25920
cagcacttcg gctttctcgc ccttgccgtg gtcgaaggtg atcacgtcac cggcgacgag    25980
gctggacagg cgctcggcgg tttgcagggc ggcgaccgct tcgttgtaga cctcggtcag    26040
cttggtcagg gcgctatggt ggaagaccac gttgttgcgg aagtcctcga cggtggccgg    26100
cttcttgatc agcttggcac ccaggacagc agcggtggtg gtttcggtgg tggtgttgac    26160
gttggtcatg ttgtagctcc tcagttgagt tggatcgcgg caaggaatgg ccacggtgga    26220
aggctggcgc gccagccttc gccttggtca ctcggcggtg atcgtcactt gggtgccctt    26280
gtcgacgagt accatgcgcc aggtatcatt gcgcagcaca gtgggactcg ggtggacagg    26340
ttgccctcga cttcatcgtg gatgactaca ggcatcgtcg tgcggacgcc ccggtcggtc    26400
gtgctcccca cgccgagcac cagcgtgcct cgacgggact cgggctgcac cacacggtac    26460
agctcacctg cctccaattc ggtgtgccga tacaggcggg tcggtacgag gttggcattg    26520
tgggtatggg tacggatcat tccgtcagct cctgtagtta cttgatgttc aggtggcgct    26580
```

```
tcagcccggc caggaggccc cggtacacgg cgcgcagcgc caggaatatt ccggcgatga    26640
tcacgagtgg ccagacgcac ccgattacgc atgcgtcctg gaactgcact tccgtcgggt    26700
tctcgaacgg tggcggcgcc actgcgatgc agtagcaggc acctgccagc aggccgaggc    26760
agcagtacag gccgagtacg aacagggcag cgatcattgg tcggcctccc cttgcacgag    26820
cttgatgtac tcgccggcac ccaggcggcg gcaccgccag tctgtgttta gtatggccgt    26880
gcccaccgcg tactgcgcgg ggttcatgct gtgcagtacg atggctgcct gggcgagggc    26940
aggcgtctgc ttggtcgcca gcacaacggc gccctctgcc gagctaggcg tcaccacctt    27000
gtagagttca cctggggaca ggcgccctac ggacaagact ggtggcgccg ggtcttcagg    27060
cttgacatac acggtcttga cggccattac tcgccccccct gtacacaatc ggtacggaag    27120
acctcctgga cttcgaaggc cgggtagagg gccaccgccc ggctgtcccg ccacagctct    27180
acgaaggtat cactggcgac cacgtaatcg gcctgcacct ggcgggtagt tccgtcggtc    27240
agtcggacgg tatagctcgg tttcatatgc gcttgctcca gttcacgatg aggaaccggc    27300
tcccaagcaa ggccgtgcgg cgatgcttgc gaagccagcg tttagctgcc ttgcgtgagt    27360
agaatcgcaa gggacgtacc gggcgcttgc gactccacac gaaggcgcaa ccgcccgacg    27420
ggctgacagc gatgatgagc cacgtcattt gcgggtcggt agctgtctga tgaaccgcac    27480
gttacgggcc tcggcctcga tcaggcgcag ggtccgctcg cagcgtacgt ggtagatcgt    27540
catacagcgc gacggtcggg ttatggcttc aatgatgccc ttggtgcctg ccgcgtcggc    27600
acccaggtag cggtcgctgt agttcaccag ccccacgcgg tggccgatac ggtagggatc    27660
acgcgaggac atggtacgag gtccctgcaa tgtcgaagat cgggcgcccg ttcgcgcagc    27720
ccttgcggta ttcagcgttg atccatccgt acgcctggca ggtgacacgc ccggacagcg    27780
ggctgccctg gaccagcagc acgtcgaagc cttcggagtc gaggttccgg ctcatacgat    27840
acgcttcgtc atagcggttc acagtcacgc cggcgcccac taccacgaac ccgcctgggg    27900
tcaggacgtg cgcggtattc aggtcaccca tgccggaatcc gtgggcgcac agcaccttgt    27960
cggcggcgtg catgcctgcg gtcgggtcct tggggattgc aatcaacagg gtattcaaag    28020
cttgcatggt ttagttctcg cttgtgatga gtccagcgat ggccccggag taggcgaggg    28080
tcgcccgcca gggccatgac ttgagtcacc gattcagcat caggtggatg aacagggcgg    28140
cggcgatcat gccccagggtg aattgagtgg cccactcgct aacgttcagg ccgaactcga    28200
agaaaggtag agcgatccag atatccatta ctttgcctcc tgtacggctt gctcgccgta    28260
gggatagtgg gcgggacggc tgtactgagc cagggcgatt tgacgttgca ggcgttgctt    28320
gaagctcatc gggttatctc cagttcacta ggtccagcgg agcgcccgcc ttgcaggcgc    28380
tcgacttgag ctagttagtg ggtagcagcg cgcttggctt gctcgaccat gggcgcagcc    28440
ttggcggcca ggacttccag gtcgcccagc agttcagcgc cgacgatcac cttgcccttg    28500
gtctgagcct ggagcacttg cttgcggaca gcggccagcg cagcggcgag gttgaactcc    28560
tgatcgaggg acttctccgg cttgcagccg taccacggct ggtcggtggc gccgacgaga    28620
tcggtcttgc cgaacttgtt gaacaggaat ggatgctcct tgttggtttt cttgtcggta    28680
ttcacctgta ccttgccgaa catggtcagc cactcgacca gagcattgcg gcggctgccc    28740
ttgggcatgg cttcatacag cgccttgact acggtcacgt cgccatggag atcgacgtgg    28800
ttgaggatcg acaggccggt cagttggatg gcctcgtcca gttccttgcc acgaacgcgg    28860
atggcttcga ttgcgttggt gatggcagcc ttgccgacga aagcgataac ggttttggtc    28920
agttggttgg tcatggtgtt acctcagatg gttttgttca ggtaagcagc ggcggccttg    28980
```

```
tagccttcgc tatgtggagt ggtcaggcgg tcaacccgcg ctggccggtc ttgctttact   29040
tcacgctctt gaaacacggt gagatcgtta cgcacgctac tgcggaatgc gcagtcgtaa   29100
cgacgctcac gttggcgtct ggtcttagct cgcttgcgct gagctggcgt cagttcattc   29160
acccgtggca ttacaagccc ctcccttgag actgcttggc gttccatcct ttcaggatgt   29220
tgcgtgcctt gccgtcgcta cccttcacga acgacttctg gtccggggttg tggtagcgtc   29280 caggcatcgg ctccgggtcg gtagagtacc gcacgtcacg catcttgcgc agttccttgc   29340
ggctggtcac gtcgtcctga gcgatgagct tgtcgcgctt agcttcccat gaagaccagt   29400
aagcctcttg agcttgccag ggttgcttgg gtgccttcgc cttgaagtgt gccatcggca   29460
atcctcacta ggtctgtctc ttgaatcccc tcggtggaag ggcctcaagg gacaaacctt   29520
ggcattggca tagtccctgt agtatcagcg gttctggctt gtcctgcgca tactattcgg   29580
gatcgtcagc actcttcccc cgtacccttt gcgctatctg cctggccttg ttcaatcggc   29640
ccgccgatac tacccagcat actgtcagtc gcgattaacc gaggtttcta gttctcgatc   29700
ccactgacac tctgttcgtt cccaccggca ctaacgtgcc tttgcttaac cgtggacggg   29760
gaggcttccc gctcagactc ttttgggtga gtcttcagca cccgacaggt attccctggg   29820
accctgccta accagttgca gcttcagtca acctaccgca ccagtccatg taccgctggt   29880
gaagcttcga acctctaccg ccagatggct cagccatcct ttcgtcttgc tgcgcatgtt   29940
agagacttgc gcttgtcttg tcaatcctct gtcggggatt agttcgtcca gttctctggc   30000
ataggccctt ttgctgagtg gccatcagtg gtgcgaactg taccgcgtgt cctgcaccgt   30060
gtcaatcccc tcagtgatgc ctgccggcct tacacactgc ggttcctgcc ctaagagttt   30120
gccgtgtccc ttgcgcctat ggcttgtgcc gcgcttggaa ggttgcaatc tcccgtcgtt   30180
ctggctgcgc actctaccga tgtcctggca gtgtgtcaac cctgtctcca ggctgcccgt   30240
agaggcggta ttgcgtgaag acagtgcgaa ctctacagac ctaccgccca cgtgtcaata   30300
cccgcgccag ggcgctccct ggagccttcc cacgcgtata gagacccacg cgtgcgaggc   30360
ttagtctggc tagccaggat tatcgttccc aggtaacgca aatccaccac ccagggagca   30420
gccacccagc caggaccacc accctgaaac ccgcgtggca ctaaggctgc ggttatgtca   30480
cacacaatgg acaaataggc gtccatcagc gccgcaggtg cgaccgagca ggcgagggag   30540
tggcgaggca agaccgcagg accagcggca cgccaggga ggtagaccag cacccaggga   30600
gcaggactag acaaggcagg tagaggcgag tagagtacgt ggcctagagg gagtggccag   30660
gcaaagccag gaccacccag ggagtaccca ggtagagcca caagaggcaa taccacaaga   30720
ggcaaggcgt agcgtagagg caaggccagc cactcccgca ccaccaccag accagagacc   30780
agagggcaga ggcccaggga ggaacgagat gctgagcaga caggacaggg aagccagggc   30840
atggcaccag caggacgcgg cgtggcagcg gatgctggtg gcagagcgac tagagtggcg   30900
caagtccagg gccgactgga ggcgggagta cctcgccgac cggatagcag cccaccgcag   30960
ggcaatggcc cacgccaggg catcgggagc agcctaccag ccccagggtt gaccaggggg   31020
ttgacaccag cgacgaaccc tgtagaatgg gcggcgaagg gcgggaagcc cacgccaccc   31080
ggcgaagccg gaagctccca ggaggctagg cagcaccacc caggcaacac ccaggcgatg   31140
gcccaccagg cggagggcct acggggggaag gatgggcgtg ttggagtcgg gagggttctc   31200
acacgacgat atcaaaattg gacccggagt aactactccc acccacacca gccaacccag   31260
cccacacaca ccctcaataa aaattccagt agttccagtg gagcacccaa ctatgtaggt   31320
```

```
gctcggcttg agctactcga tcacttatag accagggcct tggcagtctc gacagcagcc    31380
atcagctcgt cgagatgcgc gaccagttca gcgcgcagct tggtctcgtt gtagccagaa    31440
cccagggccg cttcttccag cggacggatc aggttctcga tggtgccggc gaaggcgcgg    31500
aggtctttct gagttgcagc ggcgaaggtt gccatggttc agttccttgt gttatggatg    31560
gagtcaggtt ggacgggcct gtagctcagc ccgccggtgc ggtgtatacg accttggtga    31620
tagcaccgtt ggctacggtc accttcacgg aaccaccgcc gtccacgggc agggtgtcac    31680
cgttcttcac cttgtaggcg gtgagcgggt ccggtggagt agcgccaccc tcgccgccca    31740
gggcggtggc tgctgcgatc acagcggtgg ccttggcctt gacatcggcc tcgtccatgt    31800
cgtgcagggc gatgcggttg tcggtgccgg gctggcagac ctggtagaag gtcaggccgg    31860
tgttacggcc agcgaggtat tgctcacggg tgttcgccat gtcaatctcc ttgattcaag    31920
gcgttgcata ggtccagggc gtcctgatag gccgctacag cgcggattag gccagcctgg    31980
gtggtagggt caattagtgg gtgttcgcac agcacagcgg gcgccggggc ggttgcacag    32040
gctgtcaacg acagcagcag gcacaggccg gtcagcccac gggcgattct ggtccagggc    32100
acggtccacc tcctggcgct gggtgttggt cttggcggca acctcctgga cgtggcgctg    32160
caaggtggca tagcgcacct ccagggcctc cgcacgggcc gtctgccgct tgatctcctc    32220
ctgggcgata cccaaggccc ggtagctctg aacgaagccg tatgaggctc ccagggctac    32280
cacagcaagg acgagtattg cgacgatggt tcgaggcatt gtttgatctc cgcgttgcgg    32340
cgattcacga ggcccttgga tacgaccttc tggccgtcga tcgtgacctt gttccacatg    32400
gccagggctt ggcagccctc agtggcgcgg ccttggttga agcgcttgaa cgctgtgctg    32460
gttgtacaga ctggacccac gttgtagcag aagaacgtca gggcggtttg ctcgttgacg    32520
ttcagcggca ccttgatggc gtccaggaca atgcgctcga agcgctgata gtccttgagc    32580
gtcatctggt agcactgctc cggtgtggct ttgtcaccca tcttgacccc ggcagtggtg    32640
ccagaacaga tggtgggtac gccggcgatg tctcggtagg cagtggtctc gctaccttcc    32700
agggcgacaa ggccggcgag ggcagccgca agggctgcgc cgcgcagggg cttgttcact    32760
tcttgaacct ccggcgaagc tccgcgatgc tatcgagcat cttcgggagc agggtgatga    32820
gctgggcgcc cacgtagagc gcggtgagta ccgcagcaca gaggctggcg atctcatagg    32880
gcgagtaaac ggcgatcccc acgcggtga tggcgagggt gcctttgccc gcctcggtgg    32940
cggtatcgag catcatagtc ttcgtccttt tgggcggccc ttgcgacgct cccggcccat    33000
gccgagagac cgaaggacag acttagtgta acccatcggg ttgttcagcc attccttctt    33060
ggcagcctct tcacgagcgc gggttgcggc ttcgtcgtcc tttacgagcg tgggtgctag    33120
ctcgcggaca aggccctcaa gggcatcgat ccgtcgtcc ttcggcagtg agcctcggtc    33180
ggtggtgatg ttgtgaatct ggtggaacac ggagcgctca ttgcgcttgt ccgctgggta    33240
ctgctgacag gccacgtggt cggaatccat cgccgatacg tggaagatca gacggtgccg    33300
ctgcatgatg ggccgcaggg tgtcgatgat acgacgctct ttctgtccgg acttctggcg    33360
gtcttctacg ccgatcccct catagcgggg cttgttggtg tccgggtcga tggatcgcat    33420 gtggttgcg aagagctgac caactgcacc agcgccgagg tttttctcga catagatcac    33480
cttgacgcca taacgcgcag ccagggcaat acatttctcc aggttctcct cggcaaagcc    33540
acccttccag ccgccgatgc tcacgacgtg gatatacggg ccaagagtcc cgcccacagc    33600
atacgacagc tcgtcgccac cgtcgccggc agggtccacg aacatcgtca tctgctggag    33660
tggtgcccag ccgccagcca tcagcgccgg caggtacagc tcaggcttga tgaccgggaa    33720
```

```
tcggtgggcg tcgaacttga gcttgaagcg ctcatcggca gcccaggcca cttgctccgg    33780
cacgctctca tgcgtggcgt cgatgaacag caggtcgcgc agcttgagct gcatacgctg    33840
ctcgtcggcg aggctggtgt ccagcatgta ctgaagctgg aagccctcgg ggccttggtc    33900
cagctccttg tcgagcaggt cctcttcgtt gtagcgctgc ggatcggcag cccagccacg    33960
ggtcccatcc aggcccttgc cggtgcgcgg gttgtggcct ttctcctcca ggcgggcaat    34020
gcgcgccagg atggaaggtg cgagccagtc accgtagcgt tcctgctcat ccagggtcgg    34080
gaagcggccc ggccagatgc gcatcaggaa gccccgcgcc ggcagaccgt tgtagatcga    34140
ctcacgggac tgcggcgtgc ccaggtagag aatcttaccg tgggtacaga tagaggtgaa    34200
ctcctgcgac tgccgcgtca gcttggcccg ctcggtggcg gtgaggccgt tcttcgtggt    34260
ctcgatgtcg tcagggatca ggatgtcagc ccggtagccc tggagggcag cggtgatccc    34320
gatgcagttg atggaggccg atttctcgac gcccttcaat gcccagttca cgtcgaagct    34380
ggtggccgag gtacggtcac ccatgcgggc ctcggggcgc aggtacgcca gaaggtccca    34440
gtgcatgatc agcttcgtga tcaactggcc gttctcctcg gccttgtcac cggagccgga    34500
taccagcatg gcgcgggtag ccgggttttg agtgatgcac cagaccacgt agatacaggc    34560
gatggtggac ttggcctcgc cacgctgtgc agcgaccatt gccttgttgg gcgagtcctg    34620
catgaagtcg gcgatgtcga gctgcatcca cgtcatcttg aagccgagga acagcatggc    34680
gtccaggcag aagtcccgga agcgcgggta catgtcccgc acctcgtggg ctatctggaa    34740
tcgttcttgc ggcgtcatgc tgcctcctag tgggtgtaca gtcgttccat ctcgtcgtcg    34800
gtctcaccgg cgatgaagcc ttccagcgcg atccggcgat tctccttctg agcctggcgc    34860
atctcctcgc ggagacgatc gatgttgatg gtgtcggacg gatcgcaggt gatctcgttg    34920
tccttgagga acttggtggc ggcagcgata tccgatgcgg ggatcgggat gtcgttgtcc    34980
atgtaccact tgaagttgcg ctcgatagcg gtgcagacca gctcgtgtag caggcccagc    35040
cgctcagcac tcgcggtctg cttcttgctc attacattct ccctcggaac aggacctgga    35100
atctccagtt cgctgccatt ccgcatttga cgataggccg ggtcaccttg ccggtgccga    35160
tgataagctc ctcctcggtg aagcgagtag agctggcccg gatgtagaag ttaccctgcc    35220
gcgtgtagca gaccagcacc tgtgcccagg cgctgccctc gggccgccgg tcgtccaggt    35280
ctgctttgat gtagtccacc ggcccaatgt tcatcacatt gcgctcttcg gtagctgagt    35340
cgaagaagtc gatgaagccc tcgccctgct tggaatacac cacgatatag ttcatgttct    35400
ggtcaaacgt gaccgccatg ctagccacgc cttcgttgat gcctggaccg atgcgggtag    35460
ttactcgatc tttttcaggt gtcaggtaga taccgtcttc gagcagctcg gcgtgccact    35520
cctggtacaa cagaccttga ctaggatctt ggatggcgat accgccatcc acgtagtcgt    35580
tacggtcgtt gatgtcccgc cggtcccgcg caccctggaa gggcacacgg gtgcggtact    35640
caccgaactt gaactgtatc ataccccggtt gaagatgtgg gtgacggtga tgtccacgcg    35700
ctctaggctg ttcttaacca gaggcgggtc cagcttgatc tccagctcac ggcccgccgg    35760
ggtttcccag cggaggtact ggataccttc cgtccagttg gcatcggcag gggcaatccg    35820
catgatctgc gcagactgtg caggcacctg ataatcccg gtcccagcag cgccgctcag    35880
gttggcggtc ttggtctggc cgttgttgtc cggcgcactt accgcagtcc aggacaagct    35940 accacggggtg ccgaactcag ccgaaggctc cggcgacagg tcgcggaagg tgcggcggtc    36000
acgcatgctc agggtgtact cgacgcccctt catcgtgatc ttgactgaac tgtctgccgg    36060
```

```
cggggcgatc cgcagggtgt aggtcacgcg aagctcttcg tccaccagca ccgtgatcgt    36120
ggtaggatcg ccgttggcgt ccttgatcag ggacctggag tacagctcat tgacaactcg    36180
cccgatgcct acttccgcca gcgcctggcc ttggaaggag ccagccctga aggtgcctgt    36240
gcccgtgtgg actttctcac cggtggtgga gtcccacacg gcgcgggtgc cgtagttcag    36300
cgaggcactg gcgttagcta ccggcgccac gagggatacg tcggcgggaa ccggagtacg    36360
gttgccggtt ccggcgaaca tgttcgtcca gccgccactc gggacgcctc tggaactcat    36420
gtcttcaagg gccttgttgg tgatcaggtt tttgaagtgc aggtgctgac ggacggtgcc    36480
gtcaggacgc acaatctcca gatcgaactc gccccggata gtgctgctat ggtacataaa    36540 cttcccctc tgtgatctcc atagtcaagg acccaacctc ggaccagtgg gagtacggga    36600
taaccgattg cttgtgctcg ccggcgatga tgttcatcgc catcgtggaa ttctcctgga    36660
tcggcgtcag gaactgaact acagacttga ctgccgcgct caggacatcc atgctccaga    36720
tgctattgtc cctgacctcg gtaaggatat ggaccatgct cttcagcgta gcgtcccgca    36780
cgagcatctc gtaattgccc aggtccttac tgtccgcgaa cttcacggta tcttggatga    36840
tgccggcgac ggcatgaaac gtcatgccgc cacggtcgga ggaggactgc gggtatgtga    36900
tggtggtcag caccggcttg ggtcggcgaa tctgagacgc cacgatgcct gcgataatgc    36960
cgcgcattac tcgtcctcca tcgccccgaa gatgatccag tggttagggc cgatgcgctt    37020
gagggtacac acgccattct cgccgtagag ctgcatggtg gtgttctgca aacggttgat    37080
ggtcacgcca gggcctgcca cgatgttgag atcacgaata ccggcctgtt cgaagtggac    37140
ttcgctgaac tcgatccacg gctcgtccgg gtcctccatt tgcatggtca gggtcaggga    37200
cttgtcggtg gtgatgcagc ggttccagta accacgccag ctcggatcaa tgtccgagtc    37260
ttccgtaacg gtgcgaatct cagcgaagcc cagggcacgg cgcagcgctt cgttagcggc    37320
gtcgagtgct tcctgtgcaa ggcggcgggc ttcctcggcg atacggatcg cgtcgagaac    37380
tccgtcgagt gcgaggttcg cggtgttgat gccctcctgc acagcgtaca gcaactgctt    37440
gttgttcgcg tcgatgtacc gaggcaggaa cgggatgccc tggctgaact gagtgtccgg    37500
gacctgggcg ggcgtgtcgc ggaagatgcg gacctcttga tccttcttcg gcaccacggc    37560
caattgaatg ttggtgtcgt ctacccacgt atagtcggtg acgagtatct tatcgacctg    37620
gacgaacacg tcctcacgcc gcaggaacgg gaagtcgaga ctgaagacag cctcgacccc    37680
atctgcaacg tggatggtct cgggattctt gaaccgagcc acgttattcc ccttttgatgg    37740 attccaacag caacttggtt gccgggaaca cgttgacgaa aggcagtgcg cccgccgcgc    37800
cgttgacgat atcgccagtg gccgctgccg ggtcgtcgcc ggttacgagg tctcgaacgc    37860
ctcggaacac ttcgttggag tgttcagcca gtccgaagac cggagcagac attcgggagt    37920
ggccagtgac cacaccccac atatcggcgg tgaagcccag gccggcagtg tagccgatgc    37980
cgtcgatggc catcttgcgg atgccttcgt cagaggtgtc gaacttgccg ttgatcgctg    38040
ccttggcacc catcatcagc gctgtgagcg gatactggaa tgcgaggagc gaggccacgc    38100
caagcacgcc ggagttctcg taggttcccc ggaggagctt gttgtgcgcg aaggccacga    38160
agctgcggaa ctgcccagg atttggccga ccggcgaccg ggcgaagccc gagttctgac    38220
cgaccctgcc gtacagcagc gagtcgtcca tgatccgcag tgcggtgttc atgacggtgt    38280
tcacgtctgc ttggctccag gcgcccaat tcatcgattg ggcgttcctt cctctgtatg    38340
tgacataacc gcgaacccgc gccaacactg gcgtccagtc cacgtccttc ccgtactgct    38400
ggagcacgcg aagggctgct tcatccccct gagccgcccg cgccaccttg ttcaaggtga    38460
```

-continued

```
ggttggcgtt catacgggat tgccagttgt ggatgaactt catgccgttg agcaccggga    38520
cagcctgctt acctgcgtgc aggaagcgat ccatgaaggt atcttggctg ccaggaagg     38580
tgtcgaactg ccgcttccag ggcttcatcc ggatatcgtt ggcgaggttc aggccgagga    38640
cggtctgcat ctcgtcagcg aggtccgggt cgcgacgcat ggcgcccacg aagtctccca    38700
ggcgggagtt cagcatggcc ttcatgacgt tgaagacgcc ttgacggtgc gccattgtgg    38760
ccagctcggc gagctgatac acgcctgaga atcccagcat ggtggcgctg gtcaggccgc    38820
tggcccgctg agcaaccggg ccgagctgat gctcccttgg cacgttgccg gtgaagtccc    38880
cgaagactcc ccgcagttgc cccgtcagct cctgcacctt atcggtgccc aggtgggctg    38940
cctctcgctg gtactcccgg atgaaggctt cgatctccga gtccccggc atgcctgcgc     39000
gggccaatgc tgagcggccc gacatactgc cggcgtagtt ctccatcagc cggtccaggt    39060
ctcggtcgat caggtcctgc acccgataca cggtgccgtt gtggttgatc tcggcggtca    39120
tgtccagcga cagccggccc ttgccgtact tgacggtgcc ctggtcggac tgcttctgct    39180
cgatcttggc catgatgctg tcgaacttgg cctgggacac gttggcctcc tccagcgcct    39240
gccggatgaa tgccgtgtcc gccacgccca tcgctcccat gaactcggag cggattccgg    39300
tggcccgatc ccgcgcccgc tgcacaatgg cctgtgcgat ggtatcggcg tcggcgcgct    39360
ccagcccagg gatgccacgg aacacggcct cgctgatggc acggcgggcc aggccagggg    39420
cggcctcgtc catctgcgcc atcttcgacc agttccacga gcggtggaag tatcccggtc    39480
gcggtgcgaa gttctcgaac ccgcgcaccc cggcttccct ggcacgctgg cccatcagac    39540
catgaatctc gtctgagcgg tcggccaggg ccttgatggt cggcggtagg ttagggtcca    39600
cgcggacgct gccgtaggcg gtccactccc ggtcccggcg cagcagctcg cgggtgacct    39660
gctcgttgag ctggtcccgg actgccatgg cgcggcggga gttcagcgca cgtgccgtca    39720
ggcccacacc ctgctcagcc attgccttgg ccatcatctc gtcgtaggac ttcacgtaac    39780
cctcgaactc gttccgatag cggcggagat agctcgctgc gttgtcgttc gtgctgaacc    39840
catcccgacg taccgggtcg tcgataagac ggctcaggag tcgccgtgcg ccctctccag    39900
gctgtgccag gaggtctgcc tcgctgaaga acctgttcac gaagccggca ccctcacggg    39960
cacgttcacg ggtggtccgt acgatggtct ccaggctggc ctcctcggtt accggagcgc    40020
ccttgttggc ccacttggcc tgcgccttag tgtagccggg catggcctcc ataatcgtct    40080
cagaggcggc caggacgcgg ctcagggccg tgtcagcatc ggaccgcaga cccagtaggg    40140
tgcggatgcc ctccacgaag cgggaccaca ggcccggccc gccgtcactg tagcggaggc    40200
ggttcagggt ccgttggaag cgggtatccg tcaggcccca ggctaccagt tccttgacgt    40260
tggccagggt gttggagtta ccggctagca gcgtctcttc gaactcggac agttgccgac    40320
cggcggcgcg gtcctgcttc agggcgttga gcacgttacc ccggacgttc tccagggtct    40380
gcatggcctg agccaccttc ggactcatcg cgccaggatt ccgcaaggcg gcgttcatca    40440
cgcccacggt agcagcgtga accgcctcgt ggagcacggt caccgggttg gtgccaactc    40500
ggccaggtgc ggtgctgccg cgtacctgga ccaaggtgtc gaggccctgg gtggagtgaa    40560
tccccgccgt accaggtttg aggaaggcag agctggcagt gtcaccgccc tgcaccacac    40620
ggaacgcgct acgctgcccc aggccctcca gggtcctgat agtatcagcc accttggcgg    40680
cgatgccctg gagcggcttg ggcacctctg cgtgggtctt gaggtggtcc aggacctcag    40740
acagcttccg gcccgacagg ctatgcagct cgtcgccgaa ggcagtgtca cgtcgcggaa    40800
```

```
tagccggtat ctcagcctgc tccacgcggg cactgacacg ggatagcaca gtgccctcgt    40860
ccagcaggtc taccacgtca cctgccttga agccgcgtgc tgcggcctcc tcggcggtca    40920
tggctacttc tggcagcccg acagtaggcg ccgatacttc gggcacatgc ggttgcgttg    40980
gggcctctgc ggcaatgcgt cccgcaccag accccagcag agcacccacg ccagcgccaa    41040
gagcacccgc catgatgtag gttccggcat ccacgtcggc ccctgcggca tccagcccag    41100
caacataccc gacttgccca cgcgccgcag cagcagccat gccagcgcga ccgagccgca    41160
gagcacggcc agcgccgaaa gtaaccgcat ccactgccag ggccgccggg tccagcatgc    41220
cagccgcgaa gttccagtac gggttgtccc gtacgacttg ttcgtcctgc tcataccgtt    41280
gaatcctcga caggaggtag gccgcgtcct cggcattgcc ggcacgggcc atgatctgaa    41340
ggtagttatc agtcggctgg atacctgccg cctggagcgc ctggacccca taggtcccag    41400
cgtcgaagtt agggtccacc tcgccggtac tgttcgccgc aaggtctgcg tcgagctgaa    41460
gcgcatcgcc ccagcgtccg acgagggtgg actggttcca gagtgcggaa gcacggtcaa    41520
gggccggcag ttcctggtcc gctacgatgc gttccagttc ccgcgcattg gctcgttggc    41580
ccgctgccac gttccgttct ccgatctcgc caccgtcag gcgtcgaac cccacggtag    41640 gcaccgcgtc gagttggccc tgtacttggg cctcgtcgag ctgtgcttgg tcaaggggat    41700
acttgggcgt catgcggccc ttgaattgct ttgccatgtc ttactccgct gttgcggcgc    41760
tgtaccaatc gacaccgatt tgactcggtg tatcgaagtg gggcgccatg cgcttgatga    41820
atgcctcggc ccggttgggc gtctgcgtgt accacttgct gtttcgcaca ccagcctcga    41880
aggcttcctt gttgcgatcc ttgatcgcct ggaaggtgtt acggaactgc cgggcacgtc    41940
cttcgcccat ctggaaggcc ataccggcca atcccaggat agaggcattg ttcgtaacgc    42000
ccagctcgtc ggccaacctc acaccctggt cgagtgcgcg gtcggtgtcc tcggcgaacc    42060
actgcgcggc ttgctcaggc gtgactgtag tgcctgcccc agcattgcca ctgcccaggt    42120
aatgccccag gcccacacta taaccatcgg catccttata cgcctcccct cggtaagcct    42180
cgaactgagc cagttccttc cgccagttga acacgtcctg cttcagcatg ccggcactgt    42240
tgcccccgtt catgcgaatg tccgtgccgc tgaccttgac gttggcaccg tactcggcgc    42300
cccgcatcgc attcagctta tccgcgttgc gcttgagcac ctcgttgccg actgcctggg    42360
gatcaacccg cgtgcggtcc agggccacac cgttctcgtc gtactcgacg gcgaggaggc    42420
tgccactggt gcggtcgtac tcgaaggcga ctaccgactt gtagccgagg agtccttcga    42480
catgcggctt gtgctgctcg gccaggacgt tccgatggt ctcggtgtcg ttggtcccga    42540
atagctgctc ggcggtggtg ccgcgaggca ggatcagcgg cgcgctatcg cggcggctga    42600
ataggtcccc ttccttcagg ttccgacctt cgcctacctg gatggtgcgg ttacgcacgt    42660
tggcggcggc gatctccagc agggcctcgc ggccgtgtc gctggtgagc agacccgcat    42720
gcttgcggtc gctggccagc cagttcgcct cgtcgatggt cgcccggcga tacatgctca    42780
ggacggcctc gttgttgctc aggtcgctct cgccggtcag catgttccag gctcgaccga    42840
agatgttgtt cacgaacttg tcgttgacct gcttaccgag gttgtccttg aatgccttgg    42900
tgttctggcc tttctcgaac tcgtccatct gcttcacgac ttcggcgttg gcgctgaact    42960
cgcgcagagc ttgagctggt gcgatgccca tcttcatctg cttgagtgcc caggccacgg    43020
cgccctgctc ggcttccggg atgccggata gcatcacgtt gcc                      43063
```

PSEUDOMONAS AERUGINOSA BACTERIOPHAGE PSE-AEP-4 AND USE THEREOF FOR INHIBITING PROLIFERATION OF PSEUDOMONAS AERUGINOSA

CROSS-REFERENCE TO RELATED APPLICATIONS

This application is a U.S. National Phase Application of International Application No. PCT/KR2018/000508, filed Jan. 11, 2018, which claims priority to Korean Application No. 10-2017-0021317, filed Feb. 17, 2017, each of which are hereby incorporated by reference in their entirety.

The Sequence Listing submitted Aug. 16, 2019, as a text file named "08162_0058U1_Sequence_Listing.txt," created on Jul. 26, 2019, and having a size of 55,055 bytes is hereby incorporated by reference pursuant to 37 C. F. R. § 1.52(e)(5).

TECHNICAL FIELD

The present invention relates to a bacteriophage isolated from nature, which infects *Pseudomonas aeruginosa* to thus kill *Pseudomonas aeruginosa*, and a method of preventing or treating a *Pseudomonas aeruginosa* infection using a composition containing the same as an active ingredient. More particularly, the present invention relates to a Podoviridae bacteriophage Pse-AEP-4 (Accession number: KCTC 13166BP) isolated from nature, which has the ability to kill *Pseudomonas aeruginosa* and has the genome represented by SEQ ID NO: 1, and a method of preventing and treating a *Pseudomonas aeruginosa* infection using a composition containing the above bacteriophage as an active ingredient.

BACKGROUND ART

*Pseudomonas aeruginosa*, which is a gram-negative bacillus, is an opportunistic bacterium that is commonly found in natural environments but is capable of causing sepsis in people who have decreased immunity due to surgery, burns, trauma, or chemotherapy. *Pseudomonas aeruginosa* is a known major hospital infection pathogen and is a cause of various diseases such as endocarditis, pneumonia, meningitis and the like. In particular, *Pseudomonas aeruginosa* infection is frequently fatal in cystic fibrosis patients, and infants are known to experience serious loss of pulmonary function when infected with *Pseudomonas aeruginosa*.

Typically, vaccines and antibiotics are used for the prevention and treatment of infectious diseases caused by *Pseudomonas aeruginosa*. Here, the effectiveness of antibiotics has been continuously decreasing due to the proliferation of antibiotic-resistant bacteria. Hence, the development of drugs for use in the prevention or treatment of infection with antibiotic-resistant *Pseudomonas aeruginosa* is urgently required.

Recently, the use of bacteriophages as a countermeasure against bacterial diseases has attracted considerable attention. In particular, these bacteriophages are receiving great attention due to strong antibacterial activity against antibiotic-resistant bacteria. Bacteriophages are very small microorganisms infecting bacteria, and are usually simply called "phages". Once a bacteriophage infects a bacterium, the bacteriophage is proliferated inside the bacterial cell. After proliferation, the progeny of the bacteriophage destroy the bacterial cell wall and escape from the host bacteria, demonstrating that the bacteriophage has the ability to kill bacteria. The manner in which the bacteriophage infects bacteria is characterized by very high specificity thereof, and thus the range of types of bacteriophages infecting a specific bacterium is limited. That is, a certain bacteriophage may infect only a specific bacterium, suggesting that a certain bacteriophage is capable of providing an antibacterial effect only for a specific bacterium and thus is capable of killing the specific bacterium alone without harming other bacteria. Due to this bacteria specificity of bacteriophages, the bacteriophage confers antibacterial effects only upon target bacteria, but does not affect commensal bacteria in the environment or in the intestines of animals. Conventional antibiotics, which have been widely used for bacterial treatment, incidentally influence many other kinds of bacteria. This causes problems such as environmental pollution and the disturbance of normal flora in animals. In contrast, the use of bacteriophages does not disturb normal flora in animals, because the target bacterium is selectively killed. Hence, bacteriophages may be utilized safely, which thus greatly lessens the probability of adverse effects of use thereof compared to antibiotics.

Bacteriophages were first discovered by the English bacteriologist Twort in 1915 when he noticed that *Micrococcus* colonies softened and became transparent due to something unknown. In 1917, the French bacteriologist d'Herelle discovered that *Shigella dysenteriae* in the filtrate of dysentery patient feces was destroyed by something, and further studied this phenomenon. As a result, he independently identified bacteriophages, and named them bacteriophages, which means "eater of bacteria". Since then, bacteriophages acting against such pathogenic bacteria as *Shigella, Salmonella Typhi*, and *Vibrio cholerae* have been continually identified.

Owing to the unique ability of bacteriophages to kill bacteria, bacteriophages have attracted attention as a potentially effective countermeasure against bacterial infection since their discovery, and a lot of research related thereto has been conducted. However, since penicillin was discovered by Fleming, studies on bacteriophages have continued only in some Eastern European countries and the former Soviet Union, because the spread of antibiotics was generalized. Since 2000, the limitations of conventional antibiotics have become apparent due to the increase in antibiotic-resistant bacteria, and the possibility of developing bacteriophages as a substitute for conventional antibiotics has been highlighted, and thus bacteriophages are again attracting attention as antibacterial agents.

As demonstrated above, bacteriophages tend to be highly specific for particular bacteria. Because of this specificity, bacteriophages frequently exhibit an antibacterial effect only for certain strains of bacteria, even within the same species. In addition, the antibacterial strength of bacteriophages may vary depending on the target bacterial strain. Therefore, it is necessary to collect many kinds of bacteriophages that are useful in order to effectively control specific bacteria. Hence, in order to develop an effective bacteriophage utilization method for controlling *Pseudomonas aeruginosa*, many kinds of bacteriophages that exhibit antibacterial action against *Pseudomonas aeruginosa* must be acquired. Furthermore, the resulting bacteriophages need to be screened as to whether or not they are superior to others from the aspect of antibacterial strength and spectrum.

DISCLOSURE

Technical Problem

Therefore, the present inventors endeavored to develop a composition applicable for the prevention or treatment of a Pseudomonas aeruginosa infection using a bacteriophage that is isolated from nature and is capable of killing Pseudomonas aeruginosa, and further to establish a method of preventing or treating a Pseudomonas aeruginosa infection using the composition. As a result, the present inventors isolated a bacteriophage suitable for this purpose from nature and determined the gene sequence of the genome, which distinguishes the isolated bacteriophage from other bacteriophages. Then, the present inventors developed a composition containing the bacteriophage as an active ingredient, and ascertained that this composition is capable of being used to effectively prevent or treat a Pseudomonas aeruginosa infection, thus culminating in the present invention.

Accordingly, it is an object of the present invention to provide a Podoviridae bacteriophage Pse-AEP-4 (Accession number: KCTC 13166BP) isolated from nature, which has the ability to kill Pseudomonas aeruginosa and has the genome represented by SEQ ID NO: 1.

It is another object of the present invention to provide a composition applicable for preventing a Pseudomonas aeruginosa infection, which contains, as an active ingredient, an isolated bacteriophage Pse-AEP-4 (Accession number: KCTC 13166BP) infecting Pseudomonas aeruginosa to thus kill Pseudomonas aeruginosa, and a method of preventing a Pseudomonas aeruginosa infection using the composition.

It is another object of the present invention to provide a composition applicable for treating a disease induced by Pseudomonas aeruginosa, which contains, as an active ingredient, the isolated bacteriophage Pse-AEP-4 (Accession number: KCTC 13166BP) infecting Pseudomonas aeruginosa to thus kill Pseudomonas aeruginosa, and a method of treating a disease induced by Pseudomonas aeruginosa using the composition.

It is another object of the present invention to provide a pharmaceutical composition for preventing or treating a Pseudomonas aeruginosa infection using the above-described composition, which contains, as an active ingredient, the isolated bacteriophage Pse-AEP-4 (Accession number: KCTC 13166BP) infecting Pseudomonas aeruginosa to thus kill Pseudomonas aeruginosa.

It is another object of the present invention to provide a disinfectant, which contains, as an active ingredient, the isolated bacteriophage Pse-AEP-4 (Accession number: KCTC 13166BP) infecting Pseudomonas aeruginosa to thus kill Pseudomonas aeruginosa. In particular, this disinfectant is effective at preventing infection in a hospital.

It is another object of the present invention to provide an antibiotic, which contains, as an active ingredient, the isolated bacteriophage Pse-AEP-4 (Accession number: KCTC 13166BP) infecting Pseudomonas aeruginosa to thus kill Pseudomonas aeruginosa.

Technical Solution

The present invention provides a Podoviridae bacteriophage Pse-AEP-4 (Accession number: KCTC 13166BP) isolated from nature, which has the ability to specifically kill Pseudomonas aeruginosa and has the genome represented by SEQ ID NO: 1, and a method of preventing or treating a Pseudomonas aeruginosa infection using a composition containing the same as an active ingredient.

The bacteriophage Pse-AEP-4 was isolated by the present inventors and then deposited at Korean Collection for Type Cultures, Korea Research Institute of Bioscience and Biotechnology on Nov. 29, 2016 (Accession number: KCTC 13166BP).

The present invention also provides a pharmaceutical composition applicable for the prevention or treatment of a Pseudomonas aeruginosa infection, which contains the bacteriophage Pse-AEP-4 as an active ingredient. Examples of the pharmaceutical composition include, but are not limited to, disinfectants or antibiotics.

Since the bacteriophage Pse-AEP-4 contained in the composition of the present invention kills Pseudomonas aeruginosa effectively, it is effective in the prevention (prevention of infection) or treatment (treatment of infection) of diseases, such as urinary tract infection, wound infection, bacteremia, endocarditis and the like, caused by Pseudomonas aeruginosa. Therefore, the composition of the present invention is capable of being utilized for the prevention and treatment of diseases caused by Pseudomonas aeruginosa. In the present invention, diseases caused by Pseudomonas aeruginosa may include urinary tract infections, wound infections, bacteremia, endocarditis, and the like.

Pseudomonas aeruginosa in this specification may be sensitive to existing antibiotics or may be resistant to existing antibiotics. Briefly, it does not matter whether or not resistance to existing antibiotics is exhibited.

As used herein, the terms "prevention" and "prevent" refer to (i) prevention of a Pseudomonas aeruginosa infection and (ii) inhibition of the development of diseases caused by a Pseudomonas aeruginosa infection.

As used herein, the terms "treatment" and "treat" refer to all actions that (i) suppress diseases caused by Pseudomonas aeruginosa and (ii) alleviate the pathological condition of the diseases caused by Pseudomonas aeruginosa.

As used herein, the terms "isolate", "isolating", and "isolated" refer to actions that isolate bacteriophages from nature by using diverse experimental techniques and that secure characteristics that can distinguish the bacteriophage of the present invention from others, and further include the action of proliferating the bacteriophage of the present invention using bioengineering techniques so that the bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspension agents, and preservatives, in addition to the above ingredients.

The composition of the present invention may be used through application or spraying on a diseased site, or may be administered through oral administration or parenteral administration. Here, the parenteral administration may include intravenous administration, intraperitoneal administration, intramuscular administration, subcutaneous administration or local administration.

The appropriate application, spray and dose of the pharmaceutical composition of the present invention may vary depending on factors such as the formulation method, the mode of administration, the age, weight, gender and diseased condition of the subject animal or patient, diet, administration time, administration route, excretion rate, and responsiveness. Usually, a dose effective for the desired treatment may be easily determined and prescribed by skilled physicians or veterinarians.

The bacteriophage Pse-AEP-4 is contained as an active ingredient in the composition of the present invention. The bacteriophage Pse-AEP-4 is contained at a concentration of $1 \times 10^1$ pfu/ml to $1 \times 10^{30}$ pfu/ml or $1 \times 10^1$ pfu/g to $1 \times 10^{30}$ pfu/g, and preferably at a concentration of $1 \times 10^4$ pfu/ml to $1 \times 10^{15}$ pfu/ml or $1 \times 10^4$ pfu/g to $1 \times 10^{15}$ pfu/g.

The composition of the present invention may be formulated using a pharmaceutically acceptable carrier and/or excipient in accordance with a method that may be easily carried out by those skilled in the art to which the present invention belongs, in order to prepare the same in a unit dosage form or insert the same into a multi-dose container. Here, the formulation thereof may be provided in the form of a solution, a suspension, or an emulsion in an oil or aqueous medium, or in the form of an extract, a powder, a granule, a tablet, or a capsule, and may additionally contain a dispersant or a stabilizer.

The composition of the present invention may be prepared as a disinfectant or an antibiotic depending on the purpose of use thereof, without limitation thereto. As used herein, the term "antibiotic" collectively refers to preservatives, bactericides and antibacterial agents.

In order to improve the effectiveness thereof, bacteriophages that confer antibacterial activity against other bacterial species may be further included in the composition of the present invention. In addition, other kinds of bacteriophages that have antibacterial activity against *Pseudomonas aeruginosa* may be further included in the composition of the present invention. These bacteriophages may be combined appropriately so as to maximize the antibacterial effects thereof, because their antibacterial activities against *Pseudomonas aeruginosa* may vary from the aspects of antibacterial strength and spectrum.

Advantageous Effects

According to the present invention, the method of preventing or treating a *Pseudomonas aeruginosa* infection using the composition containing the bacteriophage Pse-AEP-4 as an active ingredient can have the advantage of very high specificity for *Pseudomonas aeruginosa*, compared to conventional methods based on existing antibiotics. This means that the composition can be used for preventing or treating a *Pseudomonas aeruginosa* infection without affecting other bacteria, namely useful commensal bacteria, and has fewer side effects attributable to the use thereof. Typically, when antibiotics are used, commensal bacteria are also damaged, thus entailing various side effects owing to the use thereof. Meanwhile, in the case of various bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the strains of various bacteria belonging to *Pseudomonas aeruginosa*, bacteriophages usually being effective only on some bacterial strains, even within the same species, and the antibacterial activity of bacteriophages thus depending on the bacterial strain even for the same species of bacteria]. Accordingly, the present invention can provide antibacterial activity against *Pseudomonas aeruginosa* different from that of other bacteriophages acting on *Pseudomonas aeruginosa*. This provides applicability to a great variety of industrial fields.

DESCRIPTION OF DRAWINGS

FIG. 1 is an electron micrograph showing the morphology of the bacteriophage Pse-AEP-4.

FIG. 2 is a photograph showing the results of an experiment on the ability of the bacteriophage Pse-AEP-4 to kill *Pseudomonas aeruginosa*, in which the clear zone is a plaque formed by lysis of the bacteria.

MODE FOR INVENTION

Hereinafter, the present invention will be described in more detail with reference to Examples. However, the Examples are merely examples of the present invention, and the scope of the present invention is not limited to the Examples.

EXAMPLE 1

Isolation of Bacteriophage Capable of Killing *Pseudomonas aeruginosa*

Samples were collected from nature to isolate the bacteriophage capable of killing *Pseudomonas aeruginosa*. Here, the *Pseudomonas aeruginosa* used for the bacteriophage isolation had been previously isolated and identified as *Pseudomonas aeruginosa* by the present inventors.

The procedure for isolating the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Pseudomonas aeruginosa* at a ratio of 1/1000, followed by shaking culture at 37° C. for 3 to 4 hr. Upon completion of the culture, centrifugation was performed at 8,000 rpm for 20 min and a supernatant was recovered. The recovered supernatant was inoculated with *Pseudomonas aeruginosa* at a ratio of 1/1000, followed by shaking culture at 37° C. for 3 to 4 hr. When the sample contained the bacteriophage, the above procedure was repeated a total of 5 times in order to sufficiently increase the number (titer) of bacteriophages. After repeating the procedure 5 times, the culture broth was subjected to centrifugation at 8,000 rpm for 20 min. After centrifugation, the recovered supernatant was filtered using a 0.45 μm filter. The obtained filtrate was used in a typical spot assay for examining whether or not a bacteriophage capable of killing *Pseudomonas aeruginosa* was included therein.

The spot assay was performed as follows: TSB culture medium was inoculated with *Pseudomonas aeruginosa* at a ratio of 1/1000, followed by shaking culture at 37° C. overnight. 3 ml ($OD_{600}$ of 1.5) of the culture broth of *Pseudomonas aeruginosa* prepared above was spread on the culture medium (casein digest, 15 g/L; soybean digest, 5 g/L; NaCl, 5 g/L; agar, 15 g/L) of a TSA (Tryptic Soy Agar) plate. The spread plate was left on a clean bench for about 30 min to thus dry the spread solution. After drying, 10 μl of the prepared filtrate was spotted onto the plate culture medium on which *Pseudomonas aeruginosa* was spread and then left to dry for about 30 min. After drying, the plate culture medium that was subjected to spotting was cultured without shaking at 37° C. for one day, and then examined for the formation of clear zones at the positions where the filtrate was dropped. In the case in which the filtrate generated a clear zone, it was judged that the bacteriophage capable of killing *Pseudomonas aeruginosa* was included therein. Through the above examination, it was possible to obtain a filtrate containing the bacteriophage having the ability to kill *Pseudomonas aeruginosa*.

The pure bacteriophage was isolated from the filtrate confirmed above to have the bacteriophage capable of killing *Pseudomonas aeruginosa*. A conventional plaque assay was used to isolate the pure bacteriophage. In detail, a plaque formed in the course of the plaque assay was recovered using a sterilized tip, which was then added to the culture broth of *Pseudomonas aeruginosa*, followed by culturing at 37° C. for 4 to 5 hr. After the culturing, centrifugation was performed at 8,000 rpm for 20 min to obtain a supernatant. The *Pseudomonas aeruginosa* culture broth was added to the obtained supernatant at a volume ratio of 1/50, followed by culturing at 37° C. for 4 to 5 hr. In order to increase the number of bacteriophages, the above procedure was repeated at least 5 times. Then, centrifugation was performed at 8,000 rpm for 20 min in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for isolating the pure bacteriophage was repeated in its entirety until the generated plaques became similar to each other with respect to size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics thereof, the novel bacteriophage that was isolated above was confirmed to be a Podoviridae bacteriophage.

The solution containing the pure bacteriophage confirmed above was subjected to the following purification process. The *Pseudomonas aeruginosa* culture broth was added to the solution containing the pure bacteriophage at a volume ratio of 1/50 based on the total volume of the bacteriophage solution, followed by further culturing for 4 to 5 hr. After the culturing, centrifugation was performed at 8,000 rpm for 20 min to obtain a supernatant. This procedure was repeated a total of 5 times in order to obtain a solution containing a sufficient number of bacteriophages. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, which was then left at 4° C. for 2 to 3 hr. Thereafter, centrifugation was performed at 8,000 rpm for 30 min to obtain the bacteriophage precipitate. The resulting bacteriophage precipitate was suspended in 5 ml of a buffer (10 mM Tris-HCl, 10 mM $MgSO_4$, 0.1% gelatin, pH 8.0). The resulting material may be referred to as a bacteriophage suspension or bacteriophage solution.

As a result, the pure bacteriophage purified above was collected, was named the bacteriophage Pse-AEP-4, and deposited at Korean Collection for Type Cultures, Korea Research Institute of Bioscience and Biotechnology on Nov. 29, 2016 (Accession number: KCTC 13166BP).

EXAMPLE 2

Separation and Sequence Analysis of Genome of Bacteriophage Pse-AEP-4

The genome of the bacteriophage Pse-AEP-4 was separated as follows. The genome was separated from the bacteriophage suspension obtained using the same method as in Example 1. First, in order to eliminate DNA and RNA of *Pseudomonas aeruginosa* included in the suspension, 200 U of each of DNase I and RNase A was added to 10 ml of the bacteriophage suspension and then left at 37° C. for 30 min. After being left for 30 min, in order to stop the DNase I and RNase A activity, 500 μl of 0.5 M ethylenediaminetetraacetic acid (EDTA) was added thereto, and the resulting mixture was then left for 10 min. In addition, the resulting mixture was further left at 65° C. for 10 min, and 100 μl of proteinase K (20 mg/ml) was then added thereto so as to break the outer wall of the bacteriophage, followed by reaction at 37° C. for 20 min. Thereafter, 500 μl of 10% sodium dodecyl sulfate (SDS) was added thereto, followed by reaction at 65° C. for 1 hr. After reaction for 1 hr, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 min to thus separate layers. Among the separated layers, the upper layer was selected, and isopropyl alcohol was added thereto at a volume ratio of 1.5, followed by centrifugation at 13,000 rpm for 10 min in order to precipitate the genome. After the precipitate was recovered, 70% ethanol was added to the precipitate, followed by centrifugation at 13,000 rpm for 10 min to wash the precipitate. The washed precipitate was recovered, vacuum-dried and then dissolved in 100 μl of water. This procedure was repeated to thus obtain a large amount of the genome of the bacteriophage Pse-AEP-4.

Information on the sequence of the genome of the bacteriophage Pse-AEP-4 obtained above was secured by performing next-generation sequencing analysis using a Pacbio apparatus provided by the National Instrumentation Center for Environmental Management, Seoul National University. The finally analyzed genome of the bacteriophage Pse-AEP-4 had a size of 43,063 bp, and the whole genome sequence is represented by SEQ ID NO: 1.

The homology (similarity) of the bacteriophage Pse-AEP-4 genomic sequence obtained above with previously reported bacteriophage genomic sequences was investigated using BLAST on the web. Based on the results of the BLAST investigation, the genomic sequence of the bacteriophage Pse-AEP-4 was found to have relatively high homology with the sequence of the *Pseudomonas aeruginosa* bacteriophage LUZ19 (GenBank Accession number: AM910651.1) (identity: 88%). However, the bacteriophage Pse-AEP-4 has a circular genome and *Pseudomonas aeruginosa* bacteriophage LUZ19 has a linear genome, and thus there is a significant difference in the genomic topology therebetween, and the number of open reading frames (ORFs) on the bacteriophage Pse-AEP-4 genome is 52, whereas the *Pseudomonas aeruginosa* bacteriophage LUZ19 has 49 open reading frames, unlike the bacteriophage Pse-AEP-4.

Therefore, it can be concluded that the bacteriophage Pse-AEP-4 is a novel bacteriophage different from conventionally reported bacteriophages. Moreover, since the antibacterial strength and spectrum of bacteriophages typically depend on the type of bacteriophage, it is considered that the bacteriophage Pse-AEP-4 can provide antibacterial activity different from that of any other bacteriophages reported previously.

EXAMPLE 3

Investigation of Ability of Bacteriophage Pse-AEP-4 to Kill Pseudomonas aeruginosa The ability of the isolated bacteriophage Pse-AEP-4 to kill Pseudomonas aeruginosa was investigated. In order to evaluate the killing ability, the formation of clear zones was observed using a spot assay in the same manner as described in connection with Example 1. A total of 10 strains, including 9 strains that had been isolated and identified as Pseudomonas aeruginosa by the present inventors and 1 strain (Pseudomonas aeruginosa ATCC 15692) procured from the American Type Culture Collection (ATCC), were used as Pseudomonas aeruginosa for the investigation of killing ability. The bacteriophage Pse-AEP-4 had the ability to kill a total of 9 strains, including 1 strain procured from ATCC, among 10 strains of Pseudomonas aeruginosa, that is, the experimental target. The representative experimental results thereof are shown in FIG. 2. Meanwhile, the ability of the bacteriophage Pse-AEP-4 to kill Staphylococcus aureus, Pasteurella multocida, Clostridium perfringens, Lactobacillus plantarum, Streptococcus uberis and Enterococcus faecalis was also measured. Consequently, the bacteriophage Pse-AEP-4 was found not to have the ability to kill these microorganisms.

Therefore, it can be concluded that the bacteriophage Pse-AEP-4 has high ability to kill Pseudomonas aeruginosa and an antibacterial effect against many Pseudomonas aeruginosa bacteria, indicating that the bacteriophage Pse-AEP-4 can be used as an active ingredient of the composition for preventing and treating Pseudomonas aeruginosa infection.

EXAMPLE 4

Experiment for Prevention of Pseudomonas aeruginosa Infection Using Bacteriophage Pse-AEP-4

100 μl of a bacteriophage Pse-AEP-4 solution at a level of $1\times10^9$ pfu/ml was added to a tube containing 9 ml of a TSB culture medium. To another tube containing 9 ml of a TSB culture medium, only the same amount of TSB culture medium was further added. A Pseudomonas aeruginosa culture broth was then added to each tube so that absorbance reached about 0.5 at 600 nm. After addition of Pseudomonas aeruginosa, the tubes were placed in an incubator at 37° C., followed by shaking culture, during which the growth of Pseudomonas aeruginosa was observed. As shown in Table 1 below, it was observed that the growth of Pseudomonas aeruginosa was inhibited in the tube to which the bacteriophage Pse-AEP-4 solution was added, whereas the growth of Pseudomonas aeruginosa was not inhibited in the tube to which the bacteriophage solution was not added.

TABLE 1

Growth inhibition of Pseudomonas aeruginosa

| Classification | $OD_{600}$ absorbance value | | |
| --- | --- | --- | --- |
| | 0 min after culture | 60 min after culture | 120 min after culture |
| Not added with bacteriophage solution | 0.5 | 0.8 | 1.6 |
| Added with bacteriophage solution | 0.5 | 0.4 | 0.2 |

The above results show that the bacteriophage Pse-AEP-4 of the present invention not only inhibits the growth of Pseudomonas aeruginosa but also has the ability to kill Pseudomonas aeruginosa. Therefore, it is concluded that the bacteriophage Pse-AEP-4 can be used as an active ingredient of the composition for preventing a Pseudomonas aeruginosa infection.

EXAMPLE 5

Treatment 1 of Infectious Disease Caused by Pseudomonas aeruginosa Using Bacteriophage Pse-AEP-4

The therapeutic effect of the bacteriophage Pse-AEP-4 on animals afflicted with Pseudomonas aeruginosa was evaluated. 2 groups of 40 2-day-old chicks per group were prepared and reared separately, and the experiment was performed for 14 days. For 3 days from the fifth day after the start of the experiment, a feed containing $1\times10^7$ cfu/g of Pseudomonas aeruginosa was supplied in a typical feeding manner. From the last day of feeding with feed containing Pseudomonas aeruginosa, Pseudomonas aeruginosa was found in the feces of both groups. From the next day (the eighth day after the start of the experiment) after the supply of the feed including Pseudomonas aeruginosa for 3 days, a feed containing $1\times10^8$ pfu/g of bacteriophage Pse-AEP-4 was fed to chicks in the experimental group (administered with bacteriophage) in a typical feeding manner. In contrast, a feed having the same composition but excluding bacteriophage Pse-AEP-4 was fed to chicks in the control group (not administered with bacteriophage) in the same manner. From the ninth day after the start of the experiment, the number of Pseudomonas aeruginosa bacteria in the feces of the experimental animals was measured. A Pseudomonas-aeruginosa-selective medium (Pseudomonas Cetrimide agar plate; Oxoid) was used to prevent interference with other contaminating bacteria in the measurement of the number of Pseudomonas aeruginosa bacteria in this example. The sample was spread on the selective medium and cultured at 37° C. for 18 to 24 hr. Colonies presumed to be Pseudomonas aeruginosa were isolated from the selective medium, after which Pseudomonas aeruginosa was identified through polymerase chain reaction (PCR) (the case where the number of colonies identified as Pseudomonas aeruginosa through PCR is $10^2$ cfu/ml or more=2, the case where the number of colonies identified as Pseudomonas aeruginosa through PCR is $10^1$~$10^2$ cfu/ml=1, and the case where the number of colonies identified as Pseudomonas aeruginosa through PCR is $10^0$~$10^1$ cfu/ml=0). The results are shown in Table 2 below.

TABLE 2

Results of measurement of number of
*Pseudomonas aeruginosa* bacteria (mean)

| | Day | | | | | |
|---|---|---|---|---|---|---|
| | D 9 | D 10 | D 11 | D 12 | D 13 | D 14 |
| Control group (not administered with bacteriophage) | 1.0 | 1.0 | 1.1 | 1.2 | 1.1 | 1.3 |
| Experimental group (administered with bacteriophage) | 0.2 | 0.2 | 0.1 | 0 | 0 | 0 |

As is apparent from the above results, it can be concluded that the bacteriophage Pse-AEP-4 of the present invention is very effective in the treatment of diseases caused by *Pseudomonas aeruginosa*.

EXAMPLE 6

Treatment 2 of Infectious Disease Caused by *Pseudomonas aeruginosa* Using Bacteriophage Pse-AEP-4

The therapeutic effect of the bacteriophage Pse-AEP-4 on diseases caused by *Pseudomonas aeruginosa* was evaluated as follows. 40 of 8-week-old mice were divided into a total of 2 groups of 20 mice per group, after which subgroups of 5 mice each were separately reared in individual experimental mouse cages, and the experiment was performed for 7 days. On the second day of the experiment, 0.1 ml of a *Pseudomonas aeruginosa* suspension was administered to all mice through intraperitoneal injection. The administered *Pseudomonas aeruginosa* suspension was prepared as follows. Specifically, *Pseudomonas aeruginosa* was cultured at 37° C. for 18 hr in a TSB medium, and only the cells were recovered, and the recovered cells were suspended in saline (pH 7.2) at a concentration of $5 \times 10^9$ cfu/ml. At 2 hr after administration of *Pseudomonas aeruginosa*, $10^9$ pfu of bacteriophage Pse-AEP-4 was administered through intraperitoneal injection to mice in the experimental group (administered with the bacteriophage solution). 0.1 ml of saline was administered through intraperitoneal injection to mice in the control group (not administered with the bacteriophage solution). Both the control and experimental groups were equally fed with feed and drinking water. Whether or not the mice survived was observed daily starting from the administration of *Pseudomonas aeruginosa* until the end of the test. The results are shown in Table 3 below.

TABLE 3

Results of measurement of survival rate (%)

| | Day after bacteria administration | | | | | |
|---|---|---|---|---|---|---|
| | D 0 | D 1 | D 2 | D 3 | D 4 | D 5 |
| Control group (not administered with bacteriophage solution) | 100 | 70 | 30 | 10 | 10 | 10 |
| Experimental group (administered with bacteriophage solution through intraperitoneal injection) | 100 | 95 | 95 | 95 | 95 | 95 |

As is apparent from the above results, it can be concluded that the bacteriophage Pse-AEP-4 of the present invention is very effective in the treatment of infectious diseases caused by *Pseudomonas aeruginosa*.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

Accession Number

Name of Depositary Authority: KCTC
Accession number: KCTC 13166BP
Accession date: 2016 Nov. 29

---

The invention claimed is:

1. A method of suppressing diseases caused by a bacterial strain of *Pseudomonas aeruginosa* and alleviating pathological condition of the diseases caused by the bacterial strain of *Pseudomonas aeruginosa*, comprising: administering to an animal other than a human a composition comprising Podoviridae bacteriophage Pse-AEP-4 which has an ability to specifically kill the bacterial strain of *Pseudomonas aeruginosa* and has the genome represented by SEQ ID NO: 1, and is deposited as the accession number of KCTC 13166BP, wherein the diseases are urinary tract infections, wound infections, bacteremia or endocarditis.

* * * * *